(12) United States Patent
Matsui et al.

(10) Patent No.: US 8,906,644 B2
(45) Date of Patent: Dec. 9, 2014

(54) METHOD FOR CULTURE OF HEPATOCYTES

(75) Inventors: Hitoshi Matsui, Tokyo (JP); Yasuyuki Sakai, Tokyo (JP); Teruo Fujii, Tokyo (JP); Shoji Takeuchi, Tokyo (JP); Yukiko Tsuda, Tokyo (JP)

(73) Assignees: The University of Tokyo, Tokyo (JP); Mitsubishi Chemical Medience Corporation, Tokyo (JP)

( * ) Notice: Subject to any disclaimer, the term of this patent is extended or adjusted under 35 U.S.C. 154(b) by 0 days.

(21) Appl. No.: 13/392,226

(22) PCT Filed: Jul. 28, 2010

(86) PCT No.: PCT/JP2010/062707
§ 371 (c)(1),
(2), (4) Date: Mar. 7, 2012

(87) PCT Pub. No.: WO2011/024592
PCT Pub. Date: Mar. 3, 2011

(65) Prior Publication Data
US 2012/0183989 A1 Jul. 19, 2012

(30) Foreign Application Priority Data
Aug. 26, 2009 (JP) ................................. 2009-195869
Mar. 26, 2010 (JP) ................................. 2010-073486

(51) Int. Cl.
G01N 21/64 (2006.01)
C12M 1/12 (2006.01)
C12M 1/34 (2006.01)
C12M 1/00 (2006.01)
C12N 5/071 (2010.01)
C12M 1/04 (2006.01)
G01N 33/50 (2006.01)

(52) U.S. Cl.
CPC ............ C12M 23/20 (2013.01); *C12N 2533/54* (2013.01); C12M 25/14 (2013.01); *C12N 2533/30* (2013.01); C12M 41/46 (2013.01); *C12N 5/0671* (2013.01); C12M 23/24 (2013.01); *C12N 2503/00* (2013.01); *G01N 33/5044* (2013.01)
USPC ......................................... 435/29; 435/287.1

(58) Field of Classification Search
CPC .............................. C12M 23/20; C12M 23/24
USPC .................................................. 435/29, 287.1
See application file for complete search history.

(56) References Cited

U.S. PATENT DOCUMENTS

2004/0005303 A1* 1/2004 Sullivan et al. ............. 424/93.21
2006/0035376 A1* 2/2006 Geltser ......................... 435/395
2007/0299537 A1 12/2007 Sudo et al.

FOREIGN PATENT DOCUMENTS

WO 2007/021343 2/2007

OTHER PUBLICATIONS

Macklis et al., In Vitro Cellular & Developmental Biology, vol. 21, No. 3, Part 1, p. 189-194, 1985.*
Nishikawa et al. (Journal of Biotechnology, vol. 133, No. 2, p. 253-260, 2008).*
S. Kidambi et al., "Cell Adhesion on Polyelectrolyte Multilayer Coated Polydimethylsiloxane Surfaces with Varying Topographies", Tissue Engineering, vol. 13, No. 8, pp. 2105-2117, 2007.
K. Nakazawa et al., "Morphological and Functional Studies of Rat Hepatocytes on a Hydrophobic or Hydrophilic Polydimethylsiloxane Surface", Acta Biomaterialia, vol. 5, pp. 613-620, 2009.
M. Nishikawa et al., "Development of Highly Functional Hepatic Tissue Through Mimicking Spatio-Temporal Environment in the Liver", Seisan Kenkyu (Production Research), vol. 60, No. 2, pp. 152-159, 2008.
E. L. LeCluyse et al., "Formation of Extensive Canalicular Networks by Rat Hepatocytes Cultured in Collagen-Sandwich Configuration", American Journal of Physiology—Cell Physiology, vol. 266, pp. C1764-C1774, 1994.
H. Matsui et al., "Enhanced Development of a Bile Conaliculi Network in Hepatocyte Sandwich Culture with Direct Oxygen Supply Through Polydimethylsiloxane Membranes", $7^{th}$ World Congress on Alternatives and Animal use in the Life Science, Final Programme, p. 47, ID ABS: 165, Aug. 4, 2009.
English translation of the International Preliminary Report on Patentability and Written Opinion dated Mar. 13, 2012.
Supplementary European Search Report mailed Oct. 4, 2013 in corresponding European Application No. 10 81 1643.
H. Matsui et al.; "Enhanced Development of a Bile Canaliculi Network in Hepatocyte Sandwich Culture with Direct Oxygen Supply through Polydimethylsiloxane Membranes", 7th World Congress on Alternatives and Animal Use in the Life Sciences; (2009) Final Programme, Rome Italy: Aug. 30-Sep. 3, 2009, Aug. 4, 2009, p. 47—The poster, Abstract and NC3Rs.; XP002713032 retrieved from the Internet: URL:http://www.ncr3s.org.uk/event.asp?id=922 (retrieved Sep. 17, 2013).
Xingrong Liu et al.; "Biliary excretion in primary rat hepatocytes cultured in a collagen-sandwich configuration"; American Journal of Physiology; vol. 277, No. 1; Part 1; Jul. 1999; pp. G12-G21.
Masaki Nishikawa et al.; "Stable immobilization of rat hepatocytes as hemispheroids onto collagen-conjugated poly-dimethylsiloxane (PDMS) surfaces: Importance of direct oxygenation through PDMS for both formation and function"; Biotechnology and Bioengineering; vol. 99, No. 6; Apr. 15, 2008; pp. 1472-1481.
Yaakov Nahmias et al.; "A novel formulation of oxygen-carrying matrix enhances liver-specific function of cultured hepatocytes", The FASEB Journal; vol. 20, No. 14; Dec. 2006; pp. E1828-E1836 (Full Article).

(Continued)

*Primary Examiner* — Susan Hanley
*Assistant Examiner* — Damon B Bowe
(74) *Attorney, Agent, or Firm* — Wenderoth, Lind & Ponack, L.L.P.

(57) ABSTRACT

A method for culturing hepatocytes, wherein hepatocytes embedded in an extracellular matrix is placed on a gas-permeable membrane and the hepatocytes are cultured while being supplied with oxygen from the gas-permeable membrane side. By this, the polarity in the hepatocytes can be induced and a bile canaliculus can be formed in a short period of time. Further, the formed polarity can be maintained for a longer period.

9 Claims, 22 Drawing Sheets

(56) References Cited

OTHER PUBLICATIONS

Yaakov Nahmias et al.; "A novel formulation of oxygen-carrying matrix enhances liver-specific function of cultured hepatocytes", The FASEB Journal; vol. 20, No. 14; Dec. 2006; pp. 2531-2533 (Summary).

Fanny Evenou et al.; "Gas-permeable membranes and co-culture with fibroblasts enable high-density hepatocyte culture as multilayered liver tissues"; Biotechnology Progress; vol. 27, No. 4; Jul. 31, 2011; pp. 1146-1153.

* cited by examiner

Fig. 11
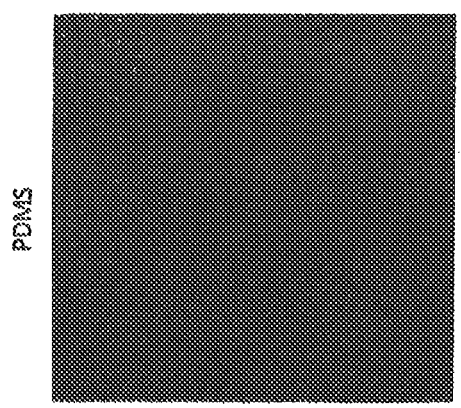
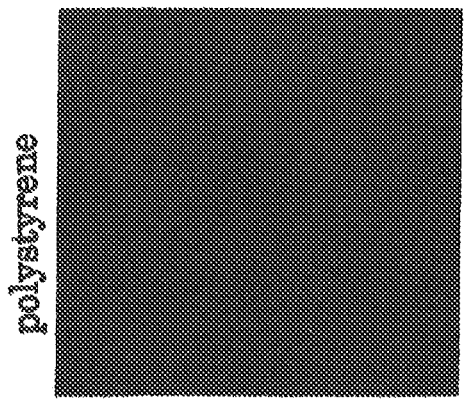

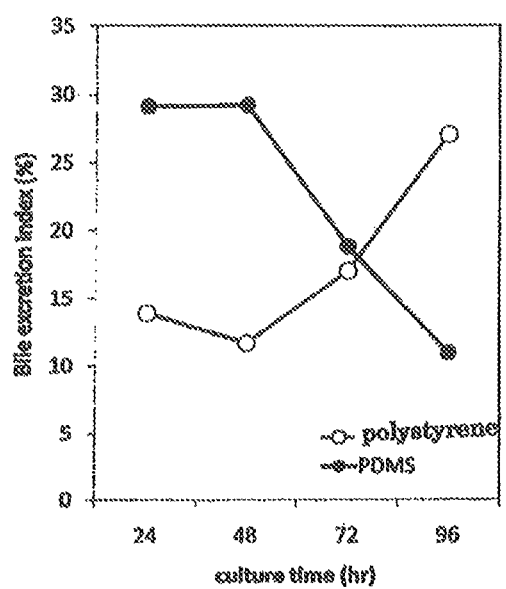

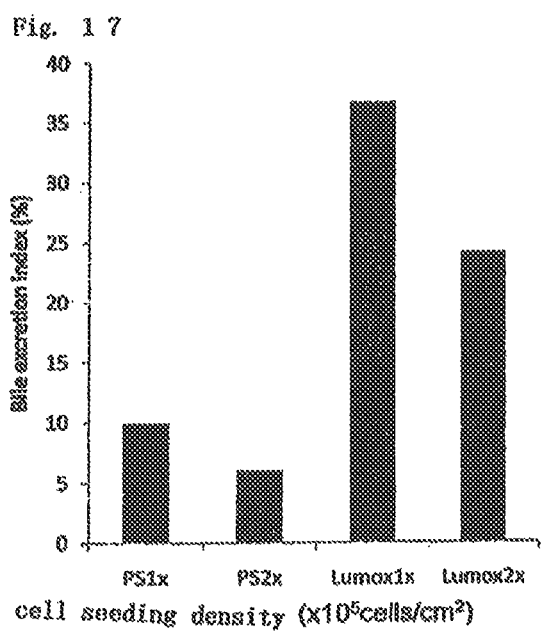

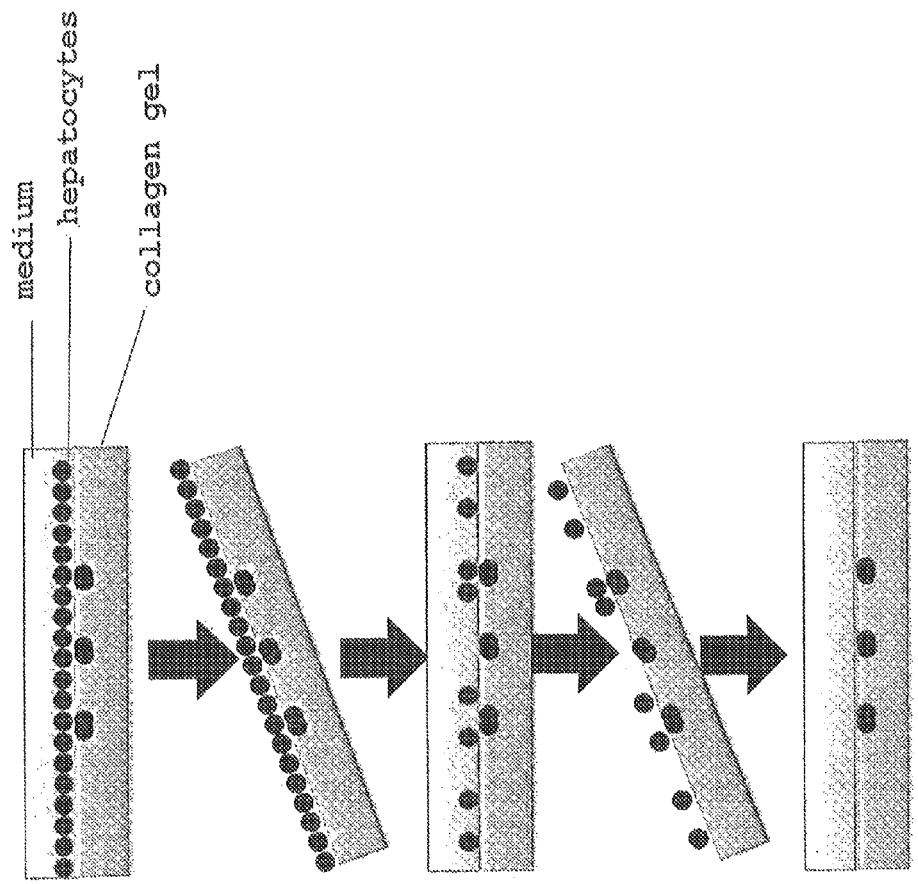

METHOD FOR CULTURE OF HEPATOCYTES

This application is a U.S. national stage of International Application No. PCT/JP2010/062707 filed Jul. 28, 2010.

TECHNICAL FIELD

The present invention relates to a method for culturing hepatocytes by which the polarity of the hepatocytes can be efficiently induced to allow formation of a bile canaliculus, a method for producing cultured hepatocytes forming a bile canaliculus by the method, a method for using the cultured hepatocytes, and a device using the cultured hepatocytes.

BACKGROUND ART

In drug discovery research, proper evaluation of incorporation, metabolism and excretion of a drug or the like in the hepatic tissue of a living body is extremely important. Further, for simply carrying out large-scale drug screening, or from an ethical point of view, an in vitro test method has been demanded. As a means for such a test, cultured cells are used, and their culture is preferably carried out under conditions reflecting those in a living body as much as possible. For example, as a culture system for hepatocytes, one which can excellently reproduce the proper polarity of the hepatic tissue of a living body, wherein, for example, the cell membrane is clearly differentiated between the blood vessel side and the bile canaliculus membrane side, is demanded For example, Patent Document 1 describes that it is thought that, by binding a binding protein or an adhesion protein to a microscale substrate and culturing hepatocytes thereon, formation of a bile canaliculus is promoted. Further, Patent Document 2 describes that, by culturing small hepatocytes on a polycarbonate porous sheet covered with collagen, a bile canaliculus-like structure was formed on Day 30 of the culture.

In the above-described three-dimensional culture methods, preparation of hepatocytes having the polarity from the primary cultured cells takes several weeks to several months.

On the other hand, in cases where the collagen gel sandwich method (Non-patent Document 1: LeCluyse et al., Am J Physiol Cell Physiol, 1994, vol. 266, pp. 1764-1774) is used, formation of a bile canaliculus and the bile component excretion activity begins to be detected about 3 or 4 days after deposition of a collagen gel. However, even in the cases where the collagen gel sandwich method is used, several days are required before the bile component excretion activity is obtained. Further, metabolites cannot be continuously analyzed in such cases since a bile duct having an outlet, as is the case in a living body, is required for the continuous analysis. There is also a problem in that the number of bile canaliculi is too small and the activity is too low, to be used in drug screening.

Further, in Non-patent Document 2 (Tissue Engineering vol.13 Number 8 2007 2105-2117) and Non-patent Document 3 (Acta Biomaterialia 5 2009 613-620), it is shown that, when hepatocytes are to be cultured on gas-permeable PDMS (polydimethylsiloxane), adhesion of the cells can be maintained for 3 days by coating the surface of the PDMS with PEM or by forming thin pillars having a diameter of 1 to 3 µm. However, the adhesion cannot be maintained for a long time and hence those cultured cells are problematic in view of stable use in a test. Further, it has been generally thought that PDMS is not suitable for adherent culture of hepatocytes.

PRIOR ART DOCUMENTS

Patent Documents

Patent Document 1: JP2008-539787
Patent Document 2: WO2005/047496

Non-patent Documents

Non-patent Document 1: LeCluyse et al., Am J Physiol Cell Physiol, 1994, vol. 266, pp. 1764-1774
Non-patent Document 2: Tissue Engineering vol. 13 Number 8 2007 2105-2117
Non-patent Document 3: Acta Biomaterialia 5 2009 613-620

SUMMARY OF THE INVENTION

In conventional methods, it has been difficult to induce the polarity of hepatocytes to allow efficient formation of bile canaliculi, and induction of the polarity took a long time and the polarity could be maintained for only a short period. Further, since it has been impossible to induce the polarity in all of the hepatocytes in the culture system to form bile canaliculi, the results varied among experiments and the sensitivity was low. Further, it is thought that, with a culture system wherein hepatocytes form closed bile canaliculi having no outlet, continuous collection and analysis of bile is impossible, and retention of bile occurs, resulting in decrease in the general liver function. With such a culture system, cultured hepatocytes forming stable high-quality bile canaliculi that can be used for a drug delivery test or for high-throughput screening could not be prepared.

The present invention was made in view of the above problems and aims to provide a cell culture method for induction of the polarity in hepatocytes quickly to allow formation of bile canaliculi, and a method for culturing hepatocytes by which the formed polarity (bile canaliculi) can be maintained for a longer time. Further, by this, the present invention also aims to provide methods that enable stable and highly sensitive drug delivery test, such as a method by the cell culture for producing cultured hepatocytes forming canaliculi, a method for using the cultured hepatocytes, and a device using the cultured hepatocytes.

The present invention provides the followings in order to solve the above problems.

(1) A method for culturing hepatocytes, comprising disposing hepatocytes embedded in an extracellular matrix on a gas-permeable membrane and culturing said hepatocytes while supplying oxygen from the gas-permeable membrane side, (2) The method for culturing hepatocytes according to (1), wherein a surface of said gas-permeable membrane is coated with collagen and said hepatocytes embedded in an extracellular matrix are disposed on the collagen-coated side of said gas-permeable membrane.

(3) The method according to (2), wherein said gas-permeable membrane is placed to form a tubular shape with the collagen-coated side facing inward, and said hepatocytes embedded in an extracellular matrix are disposed inside the tube.

(4) The method according to any one of (1) to (3), wherein said extracellular matrix constitutes a groove(s), and said hepatocytes are disposed in said groove(s).

(5) The method according to any one of (1) to (4), wherein said gas-permeable membrane is a polydimethylsiloxane membrane.

(6) The method according to any one of (1) to (4), wherein said gas-permeable membrane is a fluorocarbon membrane.

(7) The method according to any one of (1) to (6), wherein said collagen is coated by covalent bonding.

(8) The method according to any one of (1) to (7), wherein said extracellular matrix is a collagen gel or Matrigel (trademark).

(9) The method according to any one of (1) to (7), wherein said extracellular matrix is composed of a non-biological component(s).

(10) A method for producing cultured hepatocytes which form a bile canaliculus/canaliculi, comprising disposing hepatocytes embedded in an extracellular matrix on a gas-permeable membrane and culturing said hepatocytes while supplying oxygen from the gas-permeable membrane side.

(11) The method according to (10), wherein a surface of said gas-permeable membrane is coated with collagen and said hepatocytes embedded in an extracellular matrix are disposed on the collagen-coated side of said gas-permeable membrane.

(12) The method according to (10) or (11), wherein an extracellular matrix layer having a groove(s) is placed on said gas-permeable membrane, and said hepatocytes are arranged in said groove(s) of said extracellular matrix layer.

(13) A method for evaluating metabolism of a compound, comprising producing cultured hepatocytes which form a bile canaliculus/canaliculi by the method according to any one of (10) to (12) and evaluating the metabolism of said compound using the obtained cultured hepatocytes.

(14) A method for evaluating delivery of a compound, comprising producing cultured hepatocytes which form a bile canaliculus/canaliculi by the method according to any one of (10) to (12) and evaluating the delivery of said compound using the obtained cultured hepatocytes.

(15) A device for evaluating a compound using cultured hepatocytes, said device having a main body section comprising cultured hepatocytes, a compound-supplying section for supplying said compound to the main body section, and a collection section for collecting said compound or a metabolite thereof from the main body section, said main body section comprising:
a gas-permeable membrane;
an extracellular matrix placed on said gas-permeable membrane; and
hepatocytes embedded in said extracellular matrix.

(16) The device according to (15), wherein a surface of said gas-permeable membrane is coated with collagen and said hepatocytes embedded in said extracellular matrix are disposed on the collagen-coated side of said gas-permeable membrane.

(17) The device according to (16), wherein said gas-permeable membrane forms a tubular body with the collagen-coated side facing inward, and said hepatocytes disposed on the collagen-coated side and said extracellular matrix embedding said hepatocytes are contained inside said tubular body.

(18) The device according to (17), wherein said main body section further has a flow path that forms a space defined by a semipermeable membrane in the axial direction of said tubular body such that a feed from said compound-supplying section can flow therethrough, and wherein said flow path for the feed is capable of supplying the feed to said hepatocytes embedded in said extracellular matrix through said semipermeable membrane.

(19) The device according to (18), wherein said collection section has: a tubular body formed by placing said gas-permeable membrane having a collagen-coated surface to form a tubular shape with the collagen-coated side facing inward; hepatocytes disposed on said collagen-coated side inside said tubular body; an extracellular matrix embedding said hepatocytes; and a passage(s) formed by a bile canaliculus/canaliculi of said hepatocytes.

(20) The device according to any one of (15) to (19), wherein said extracellular matrix constitutes a groove(s) and hepatocytes are disposed in said groove(s).

(21) The device according to any one of (15) to (20), wherein said gas-permeable membrane is a polydimethylsiloxane membrane.

(22) The device according to any one of (15) to (20), wherein said gas-permeable membrane is a fluorocarbon membrane.

(23) The device according to any one of (15) to (22), wherein said collagen is coated by covalent bonding.

(24) The device according to any one of (15) to (23), wherein said extracellular matrix is a collagen gel or Matrigel (trademark).

(25) The device according to any one of (15) to (23), wherein said extracellular matrix is composed of a non-biological component(s).

(26) The device according to any one of (15) to (25), which is for evaluating a compound metabolism.

(27) The device according to any one of (15) to (25), which is for evaluating a compound delivery.

The present invention is characterized in that hepatocytes embedded in an extracellular matrix are disposed on a gas-permeable membrane, and the hepatocytes are cultured while being supplied with oxygen from the gas-permeable membrane side. Preferably, by allowing hepatocytes to adhere to a high gas-permeable material which is coated with collagen and embedding the hepatocytes in an extracellular matrix, the polarity can be efficiently induced in the hepatocytes. It is considered that, in a hepatocyte population cultured like this, sending and receiving of a polarity-inducing signal having a high activity can be stably achieved between the hepatocytes and cells in the vicinity, the extracellular matrix or the like, leading to induction of bile canaliculi in a broader area and maintenance of the polarity for a long period. By this, long bile canaliculi linked to hepatocytes can be maintained for a long period. Further, a drug delivery test can be carried out in a short period of time at a high sensitivity.

The "embedded" state means that the vicinity of the hepatocytes is surrounded by at least one layer of an extracellular matrix. As long as bile canaliculi can be efficiently formed, the extracellular matrix may be either continuous or discontinuous.

BRIEF DESCRIPTION OF THE DRAWINGS

FIG. 11 is a diagram (photographs) showing results of localization analysis of the MRP2 protein.

FIG. 14A shows comparison of BEI between a culturing device having a PDMS membrane to which collagen is bound by adsorption and a collagen-coated polystyrene plate.

FIG. 17 shows comparison of BEI between a gas-permeable membrane having a fluorocarbon membrane, and a polystyrene (PS) plate.

EMBODIMENTS FOR CARRYING OUT THE INVENTION

Figure 1:
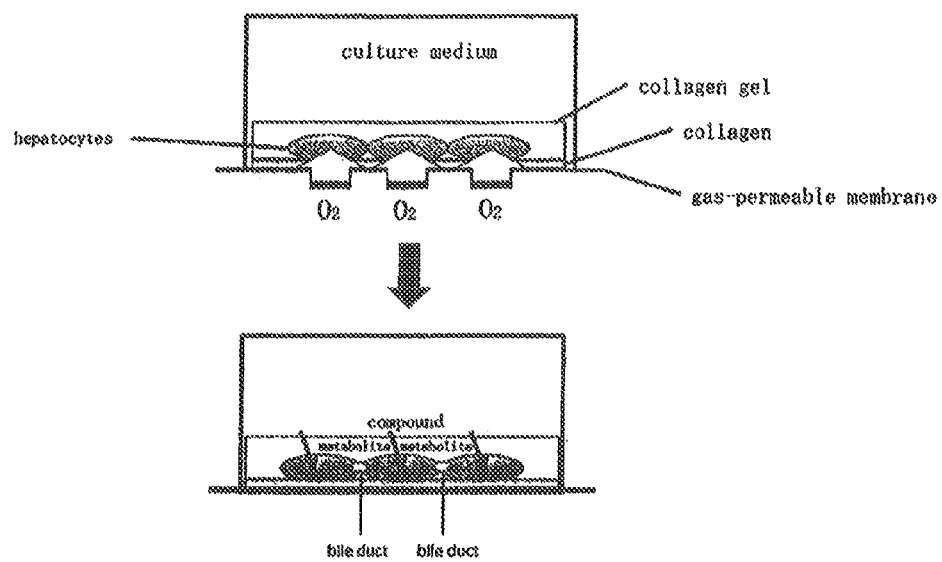
FIG. 1 is a schematic diagram showing an embodiment of the method of the present invention for culturing hepatocytes.

In the method of the present invention for culturing hepatocytes, hepatocytes embedded in an extracellular matrix are disposed on a gas-permeable membrane and the hepatocytes are cultured while being supplied with oxygen from the gas-permeable membrane side. Preferably, hepatocytes are allowed to adhere to the collagen-coated side of a gas-permeable membrane whose surface is coated with collagen, and the hepatocytes in the state of being embedded in an extracellular matrix are cultured while being supplied with oxygen from the gas-permeable membrane side.

The gas-permeable membrane to be used in the present invention is not limited as long as it allows permeation of oxygen gas, and the membrane is preferably porous and highly hydrophobic. Examples of the gas-permeable membrane include polydimethylsiloxane (PDMS), fluorocarbon, polytetrafluoroethylene (tetrafluoride) and polyurethane, and derivatives and analogs thereof.

A method for preparing a PDMS membrane is described in a Non-patent Document (M Nishikawa et al. Biotechnology and Bioengineering, vol. 99, pp. 1472-1481). However, the method for preparing a PDMS membrane is not limited thereto, and the membrane may be prepared by a commonly-known method for preparing a membrane. Examples of the commonly-known method which can be used for the preparation include a method by coating with using a bar coater (the bar coat method) and a method by coating with a gap coater (the gap coating method). Also in cases where another material is used, preparation of the membrane can be carried out in the same manner.

Further, a culture plate having a culture surface on which a fluorocarbon membrane is placed, such as Lumox (manufactured by In vitro systems and services) may be purchased and used as appropriate.

The gas-permeable membrane is preferably as thin as possible in view of the gas permeability, and a thickness of 50 μm to 2.0 mm is appropriate. However, the optimum thickness of the membrane varies depending on the durability of the material and the use of the membrane, and hence is not limited to the above-described range.

In an embodiment of the culturing device having a gas-permeable membrane, the whole culturing device may be constituted by the gas-permeable membrane, but the embodiment of the device is not restricted thereto as long as at least the portion where hepatocytes are disposed is constituted by the gas-permeable membrane. The embodiment may be modified as appropriate depending on the embodiment of the culturing device.

The collagen covering the gas-permeable membrane may be one prepared by a known method, or a commercially available collagen solution (e.g., rat tail collagen manufactured by Becton, Dickinson and Company) may be used to cover the membrane at a thickness which allows permeation of oxygen. Further, as the method to cover the gas-permeable membrane with the collagen, a known method may be used. Examples of the method include a method wherein oxygen plasma treatment is carried out to make the collagen adsorb to the gas-permeable membrane, and a method wherein a chemically reactive functional group is used to form a covalent bond. The method of binding of collagen to the PDMS membrane using covalent bonding may be carried out according to, for example, the method described in a Non-patent Document (M. Nishikawa et al. Biotechnology and Bioengineering, 2008, vol. 99, pp 1472-1481). The method by covering the gas-permeable membrane with collagen by covalent bonding is preferred since this method enables efficient preparation of hepatocytes stably forming a bile canaliculus for a long period.

On the other hand, since the efficiency of formation of a bile canaliculus in a short period is the same between the cases of covalent bonding and bonding by adsorption, either of these may be used for short-term measurement. As long as a bile canaliculus necessary for the test can be formed, an optimum bonding may be appropriately selected depending on the culture conditions of the hepatocytes.

The hepatocytes which can be cultured may be derived from any animal, and examples of the animal include human, monkey, dog, cat, cow, pig, miniature pig, hamster, ferret, rabbit, rat and mouse. Isolation of hepatocytes from the animal may be carried out according to a known method. The origin of the hepatocytes may be any of a fetus, neonate or adult. Further, hepatocytes whose differentiation was induced from embryonic stem (ES) cells or induced pluripotent stem (iPS) cells, or from umbilical cord blood, bone marrow, fat or blood-derived tissue stem cells may also be used. Induction of the hepatocytes from these cells may be carried out according to a known method.

The cell density at which the cells are to be disposed is not restricted as long as the cells can be normally grown at the density. The cells are preferably plated at a cell density of 0.1 to $12.0 \times 10^5$ cells/cm$^2$, and the cells may also be plated such that 2 to 3 layers are formed by the cells. A preferred cell density is appropriately set depending on the culture conditions, culture instruments to be used, and the like.

Examples of the extracellular matrix in which hepatocytes are to be embedded include those which may be used in the known collagen gel sandwich method. For example, collagen I, fibronectin, laminin, vitronectin, gelatin, elastin, proteoglycan, glucosaminoglycan, chondroitin sulfate, dermatan sulfate, heparan sulfate, heparin, keratan sulfate, Matrigel (trademark, Becton, Dickinson and Company), growth factor (basic FGF, EGF, IGF-1, PDGF, NGF, TGF-β or the like), or a mixture thereof may be selected appropriately to be used as the extracellular matrix. For efficient preparation of hepatocytes forming a bile canaliculus, collagen gel or Matrigel is preferred, and, for stable and long-term preparation of the cells, collagen gel is more preferred. The extracellular matrix may be prepared according to the method described in (Non-patent Document 1: LeCluyse et al., Am J Physiol Cell Physiol, 1994, vol. 266, pp. 1764-1774). In this case, the thickness of the extracellular matrix layer in which the hepatocytes are to be embedded may be appropriately selected in view of the nutrition and the permeability of the layer to the test compound, and the thickness is preferably 10 to 100 μm.

Further, the hepatocytes may also be covered using a sheet of an extracellular matrix. Such an embodiment is also included in the "embedding". For example, by deposition of a commercially available collagen membrane (trade name: Vitrigel, manufactured by Asahi Techno Glass) on the hepatocytes, an effect similar to that obtained with a collagen gel can be obtained. In this case, the thickness of the sheet may be appropriately selected in view of the nutrition and the permeability of the sheet to the test compound, and the thickness is preferably 10 to 100 μm.

Further, an extracellular matrix-like substance composed of a non-biological component may be used to cover the hepatocytes. Such an embodiment is also included in the "embedding". For example, use of a semipermeable membrane such as the collagen-coated cellulose membrane described in Non-patent Document 4 (TISSUE ENGINEERING, Volume 12, 2006, 2181-2191), the porous silicon nitride membrane described in Non-patent Document 5 (Biomaterials, volume 29, 2008, 3993-4002) or the polyethylene terephthalate membrane described in Non-patent Document 6 (Biomaterials, volume 29, 2008, 290-301) can exert a similar effect as the effect obtained with a collagen gel, by inducing formation of a bile canaliculus via a physical signal, and by depositing a substance which can supply a culture medium component and/or the like on the hepatocytes.

Particular examples of the semipermeable membrane composed of a non-biological component include porous membranes of regenerated cellulose (cellophane), acetylcellulose, polyacrylonitrile, Teflon (registered trademark), polyester-polymer alloy or polysulfone.

Further, the extracellular matrix-like substance composed of the above-described non-biological component may be used in combination with the extracellular matrix.

Using FIG. 1, a simple method of the present invention for culturing hepatocytes will now be described. A gas-permeable membrane is covered with collagen, and hepatocytes are seeded thereon, followed by embedding adhered and expanded hepatocytes in an extracellular matrix gel such as a collagen gel, which hepatocytes are then cultured while being supplied with oxygen from the gas-permeable membrane side.

The side of the gas-permeable membrane which is not covered with cells is preferably in contact with a gas phase in order to allow oxygen supply.

In this case, in order to allow oxygen supply to the cells, the gas phase across the gas-permeable membrane may be the air having an oxygen concentration of 1 to 20%. An oxygen concentration between 5% and 13% is most appropriate, which concentration corresponds to that in the liver in a living body. The oxygen concentration can be easily controlled by setting of a multigas incubator (e.g., MCO-5M, manufactured by SANYO Electric Co., Ltd.).

Further, in another embodiment of the above-described oxygen supply, the oxygen may be supplied through an artificial blood vessel composed of an artificial material or vascular cells placed across the gas-permeable membrane.

The culture conditions may be those according to a known method for culturing hepatocytes, and examples of the culture medium which may be used include Dulbecco's modified Eagle's medium and Williams E medium supplied with serum, insulin/transferrin/selenium salt and dexamethasone.

The culture is carried out as in a common cell culture, under the conditions of 37° C. and 5% $CO_2$. In cases where the culture is carried out with special cells or under special conditions, the temperature and the $CO_2$ concentration may be modified as appropriate. By controlling the culture conditions, the hepatocytes can be cultured two-dimensionally or three-dimensionally, and the number of bile canaliculi can be controlled.

By performing the culture as described above, three-dimensional position information can be given to the hepatocytes.

That is, the culture method of the present invention causes polarization of the membrane of hepatocytes, and a bile canaliculus is formed along the gap between the hepatocytes, while the basement membrane is formed in the other portions. The linked bile canaliculus formed by the bile canaliculus membrane usually has a width of 1 to 2 μm and a length of not less than 100 μm. Along the bile canaliculus network, wide portions having a width of about 5 μm may be formed.

In the basement membrane, organic anion transporters and sodium/taurocholate cotransporters for incorporation of compounds are expressed. Representative examples thereof include OATP (Organic anion transporting polypeptide) 1a1, OATP1b2, OATP1b3, OAT2, OATP4 and OATP8, and their existence can be confirmed by cell antibody staining using antibodies specific thereto.

In the bile canaliculus network, major ATP binding cassette (ABC) transporter proteins are expressed. Representative examples thereof include MRP2 (Multidrug-Resistance Protein 2), MDR1 (Multidrug-Resistance 1) and BCRP (breast cancer resistance protein), and their existence can be confirmed based on the transportation activities for estradiol-17β-glucuronide, Digoxin and Taurocholate, respectively. Further, their existence can also be confirmed by cell antibody staining using antibodies specific to MRP2, MDR1 and BCRP, respectively.

Since, as shown in FIG. 1, a bile canaliculus is formed on the surface where hepatocytes are in contact with each other, a metabolic property of a compound can be tested by adding the compound to the hepatocytes and analyzing its metabolite excreted into the bile canaliculus.

That is, the compound testing device of the present invention is a compound testing device using cultured hepatocytes, which device has a main body section, a compound-supplying section for supplying a compound to the main body section, and a collection section for collecting the compound or a metabolite thereof from the main body section, which main body section comprises a gas-permeable membrane whose surface is coated with collagen, hepatocytes adhering to the collagen-coated surface of the permeable membrane, and an extracellular matrix embedding the hepatocytes.

In another embodiment of the present invention, the gas-permeable membrane may be subjected to microfabrication.

For example, the gas-permeable membrane may be subjected to microfabrication to form a groove, hollow or partition wall on a surface of the gas-permeable membrane. For example, by restricting the area and direction of adherence of cells with a partition wall prepared by microfabrication, the array direction and area of adherence of the cells, and the array direction and area of bile canaliculi formed by the cells can be controlled.

Further, by forming a groove or hollow (recess) with an extracellular matrix such as a collagen gel on the gas-permeable membrane and placing the cells in the groove or recess, the array direction and area of adherence of the cells can be restricted, and, by controlling the bile canaliculus formed thereby, a metabolite excreted into the bile canaliculus can be continuously collected. Placement of hepatocytes in such a manner in a groove of an extracellular matrix having the groove is also included in the "embedding". Further, by covering the hepatocytes placed in the groove with an extracellular matrix, formation of a bile canaliculus can be promoted.

The shape of the groove or hollow is not restricted as long as hepatocytes forming a bile canaliculus can be prepared therewith, and the width of the groove or hollow is preferably one that allows arrangement of about 2 rows of hepatocytes, in order to reproduce the arrangement of hepatocytes in a living body. That is, the width is preferably not less than 20 μm and not more than 70 μm, more preferably not less than 30 μm and not more than 50 μm, furthermore preferably about 30 μm. Further, the distance between the bottom surface of the groove or hollow and the gas-permeable membrane is preferably small, but the distance is not restricted as long as oxygen can be sufficiently supplied from the gas-permeable membrane. The height of the lateral face is preferably not less than 10 μm and not more than 1 mm, more preferably not less than 50 μm and not more than 500 μm, furthermore preferably about 100 μm.

As shown in FIG. 2A, on a gas-permeable membrane 11 in a culturing device A, 2 partition walls 11', which are similarly composed of gas-permeable membranes, are placed, and hepatocytes are cultured in the space surrounded by the gas-permeable membrane 11 and the 2 partition walls 11'. As shown in FIG. 2B, which is a cross-sectional view taken along the a-a line in FIG. 2A, the gas-permeable membrane 11 has a collagen coating layer 12, and hepatocytes 13 are allowed to adhere to the layer and embedded in a collagen matrix 15. Thereafter, the cells are cultured by supplying oxygen using an oxygen-supplying device which is not shown placed outside the gas-permeable membrane 11 and the 2 partition walls 11', and adding a culture medium 16. On the surface where the hepatocytes 13 are in contact with each other, a bile canaliculus 14 is formed.

The size of this partition wall is not restricted as long as adherence of hepatocytes to each other can be prevented, and, more particularly, the size is preferably not less than 1 μm.

Figure 18A:
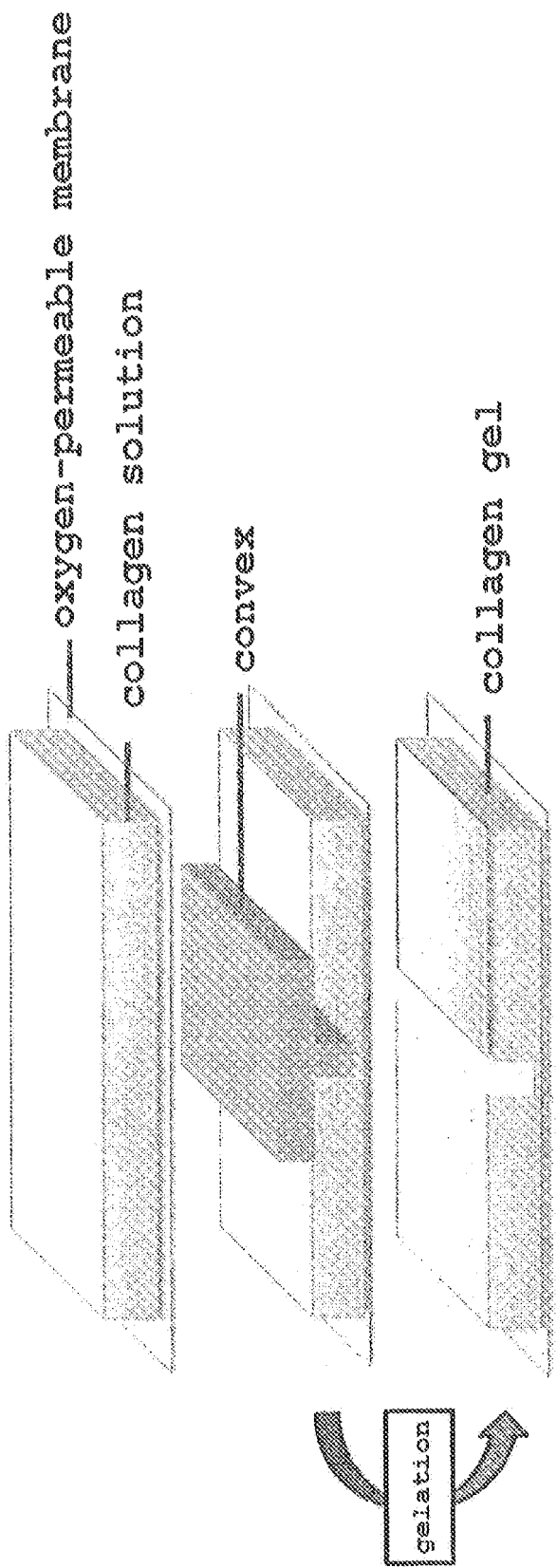
FIG. 18 shows a schematic diagram showing a procedure for preparing a continuous bile canaliculus. (A) shows a procedure for preparing a gel having a recess (groove), and (B) shows a procedure for culturing hepatocytes in the recess.

Further, using FIG. 18, an example of the method for culturing hepatocytes which forms a bile canaliculus in a groove or hollow will now be described. On the gas-permeable membrane 11 having the collagen coating layer 12 in FIG. 2, the extracellular matrix shown in FIG. 18(A) such as a collagen gel on which a groove is formed is placed. First, on the gas-permeable membrane 11, a collagen solution (at a concentration of 0.1 to 30 mg/mL, preferably 0.3 to 3 mg/mL, more preferably about 2.0 mg/mL) before gelation is placed. Subsequently, before complete gelation of the collagen solution, a PDMS mold having a protruded portion is placed thereon and left to stand until gelation, to prepare a collagen gel having a recess. In terms of the shape of the mold having a protruded portion, the width of the formed groove is preferably not less than 20 μm and not more than 70 μm, more preferably not less than 30 μm and not more than 50 μm, furthermore preferably about 30 μm; the height is not preferably less than 10 μm and not more than 1 mm, more preferably not less than 50 μm and not more than 500 μm, furthermore preferably about 100 μm; and the length may be changed as appropriate for use. Further, the material of the mold having a protruded portion is not restricted as long as the mold does not destroy the shape of the collagen gel, and preferred examples of the material include PDMS in view of the weight and ease of handling.

Subsequently, as shown in FIG. 18(B), hepatocytes suspended in a culture medium are seeded on the gel having a recess prepared as described above, and the cells are washed several times with the culture medium, to arrange the hepatocytes only in the recess, followed by culture of the cells.

After about 24 hours of culture, a collagen solution before gelation (at a concentration of 0.1 to 30 mg/mL, preferably 0.3 to 3 mg/mL, more preferably about 2.0 mg/mL) or a Matrigel solution (at a concentration of 5 to 5000 μg/mL, preferably 50 to 500 μg/mL, more preferably about 150 μg/mL) is deposited on the cells, and culture is carried out for additional 2 to 9 days. Formation of a bile canaliculus can be observed from Day 2, but a better bile canaliculus can be prepared by long-term culture. An optimum state for an evaluation test of a drug, or the like may be appropriately selected.

Further, in another embodiment of the present invention, the gas-permeable membrane may form a tubular passage having a cylindrical shape, cubic shape or the like.

That is, the culture method of the present invention also includes an embodiment wherein the gas-permeable membrane is placed into a tubular shape with the collagen-coated side facing inward, and hepatocytes embedded in an extracellular matrix are cultured inside the tubular space.

An embodiment of the compound test device of the present invention comprising hepatocytes cultured by this culture method will now be described by reference to FIG. 3A, and FIG. 3B, which is a cross-sectional view taken along the a-a line in FIG. 3A.

The compound test device B of the present invention is a device having a main body section 2, a compound-supplying section 1 for supplying a compound to the main body section, and a collection section 3 for collecting the compound or a metabolite thereof from the main body section, which main body section 2 has: a tubular body 28 prepared by placing a gas-permeable membrane 21, whose surface is coated with collagen, into a tubular shape such that the collagen-coated side 22 faces inward; hepatocytes 23 adhering to the collagen-coated side 22 inside the tubular body 28; and an extracellular matrix 25 embedding the hepatocytes 23.

The main body section 2 further has a passage 27 forming a space defined by a semipermeable membrane 26 in the axial direction of the tubular body 28. From this passage, the feed can be supplied to the hepatocytes embedded in the extracellular matrix through the semipermeable membrane 26.

Here, the material of the semipermeable membrane is not restricted as long as the material allows permeation of the compound and culture medium components, and examples of the material include porous membranes of regenerated cellulose (cellophane), acetylcellulose, collagen-coated cellulose, polyacrylonitrile, Teflon (registered trademark), porous silicon nitride, polyethylene terephthalate, polyester-polymer alloy and polysulfone.

Since these materials may be used as extracellular matrix-like substances composed of a non-biological component, the polarity can be induced to form a bile canaliculus, by placing a semipermeable membrane composed of such a material such that the semipermeable membrane covers the hepatocytes, without separately adding an extracellular matrix.

In the compound test device B, a culture medium for culturing and maintaining hepatocytes is also supplied from the compound-supplying section 1, and, when the culture medium passes through the passage 27, culture medium components are supplied to the hepatocytes via the semipermeable membrane 26. However, in the compound test device of the present invention, the culture medium-supplying section for supplying the culture medium may be provided separately from the compound-supplying section.

The shape of the passage 27 is not restricted to a cylindrical shape, and may be another shape, including a branched shape. Further, the diameter of the passage is not restricted. A plurality of passages may be provided, and a passage through which the culture medium passes and a passage through which the compound passes may be separately provided.

Further, the passage 27 and the semipermeable membrane 26 are not indispensable, and the whole content of the tubular body formed by the gas-permeable membrane may be hepatocytes and an extracellular matrix embedding the hepatocytes. In such a case, the culture medium and the compound may be allowed to pass through the extracellular matrix enclosed inside the tubular body.

Figure 3:
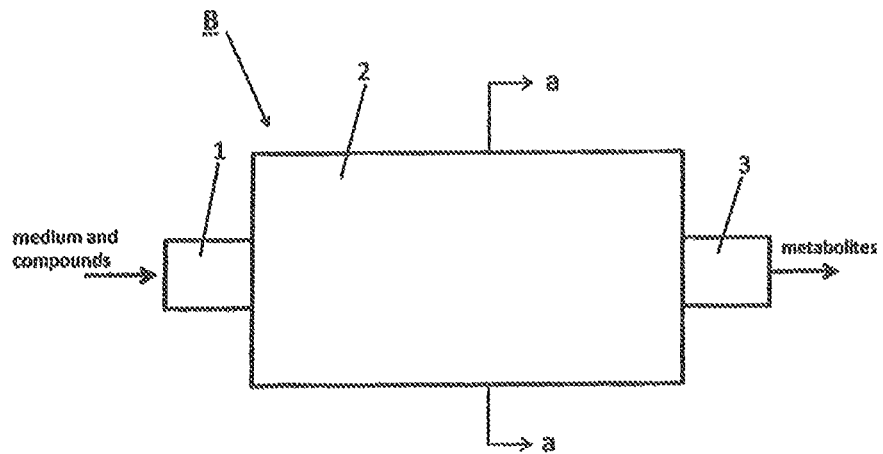
FIG. 3A is a schematic diagram showing the first embodiment of the compound test device of the present invention (lateral view).
FIG. 3B is a schematic diagram showing the first embodiment of the compound test device of the present invention (cross-sectional view taken along the a-a line).
Figure 3:
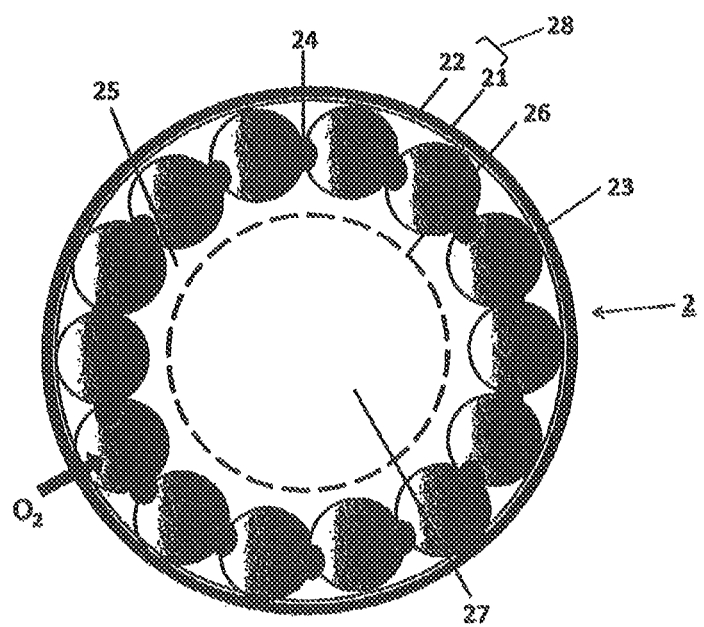

In FIG. 3B, hepatocytes 23 are arranged along the inner wall (collagen-coated side 22) of the gas-permeable membrane 21. Inside the array of hepatocytes, an extracellular matrix 25 is provided, and, further inside the extracellular matrix, a space (passage 27) separated by a semipermeable membrane 26, which is to be used for addition of a culture medium and a compound, is provided. Culturing of the hepatocytes with supply of oxygen from the outside of the gas-permeable membrane 21 causes induction of bile canaliculi 24 by the extracellular matrix. Since the phase in the outside of the gas-permeable membrane 21 is a gas phase, the concentration of oxygen that is in contact with the hepatocytes can be controlled.

By using such a device of the present invention, a metabolic property of a compound can be evaluated. That is, by supplying a test compound from the culture medium-supplying section 1 into the passage 27, hepatocytes are exposed to the compound via the semipermeable membrane 26. The compound metabolized by the hepatocytes are collected in the collection section 3 and analyzed.

The collection section to collect the compound or a metabolite thereof is not restricted as long as the section is a member with which a liquid such as a culture medium containing a compound or a metabolite can be collected from the passage or the extracellular matrix, and the collection section may have: a tubular body connected to the main body section, which tubular body has been prepared by placing a gas-permeable membrane, whose surface is coated with collagen, into a tubular shape such that the collagen-coated side faces inward; hepatocytes adhering to the collagen-coated surface inside the tubular body; an extracellular matrix embedding the hepatocytes; and a passage formed by bile canaliculi of the hepatocytes.

That is, bile ducts prepared by the hepatocyte population cultured by the method of the present invention may be assembled to form a passage (cavity), through which a metabolite can flow.

A hepatocyte culture device of such an embodiment of the present invention will now be described by reference to FIG. 4A, and FIG. 4B, which is a cross-sectional view taken along the b-b line in FIG. 4A. The cross-sectional view taken along the a-a line is the same as FIG. 3B.

Figure 4:
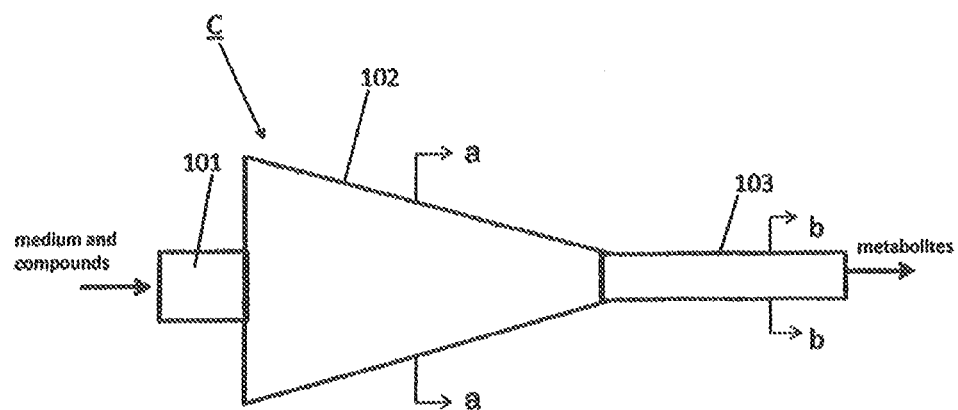
FIG. 4A is a schematic diagram showing the second embodiment of the compound test device of the present invention (lateral view).
FIG. 4B is a schematic diagram showing the second embodiment of the compound test device of the present invention (cross-sectional view taken along the b-b line).
Figure 4:
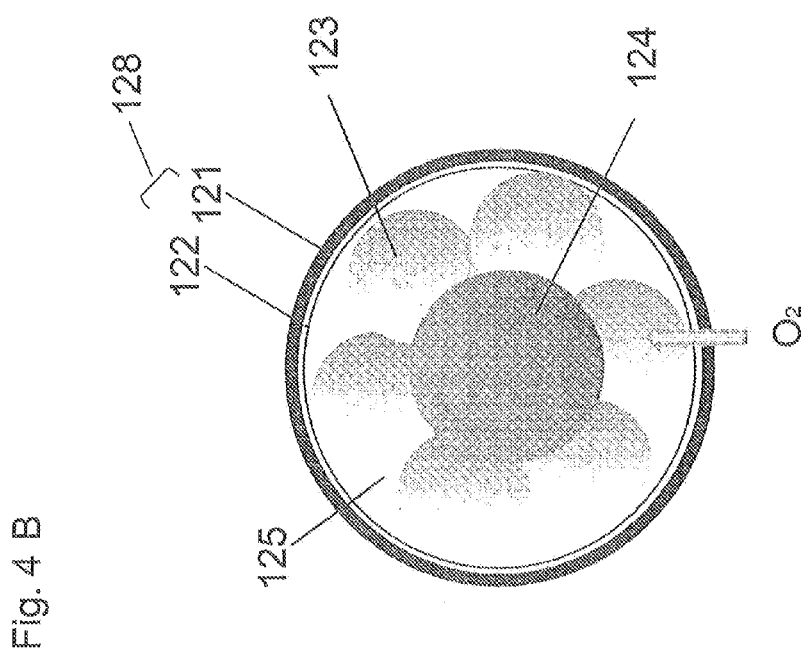

As shown in FIG. 4A, a main body section 102 is formed such that its diameter gradually decreases, and connected to a collection section 103. In the collection section 103, hepatocytes are introduced into the inside of a gas-permeable membrane such that a bile canaliculus cavity is formed at the center.

From the formed bile canaliculi, passages composed of ultrafine tubes or bile duct epithelial cells are provided, by which metabolites excreted into the bile canaliculi are discharged without delay, and collected into a reservoir for analysis.

Such a compound test device can be suitably used for a drug (compound) delivery test such as the one described later.

The hepatocytes that formed the bile canaliculi prepared by the method of the present invention can be used for a drug delivery test or a high-throughput screening of a drug candidate substance.

Examples of the drug delivery test include a test to study the amounts and the rates of incorporation of a drug into hepatocytes and the following excretion of the drug into bile. Further examples of the drug delivery test include a test to confirm whether a certain Compound A inhibits or promotes delivery of Compound B.

Examples of the method of the drug delivery test include the method described in a Non-patent Document (Liu X et al., Am J Physiol, 1999, vol. 277, pp. G12-21).

Particular examples of the method of the high-throughput screening include the following method, wherein a very small amount of a compound can be analyzed using an ultrafine passage and a highly sensitive detector, which analysis is automatically or semi-automatically carried out.

Figure 2:
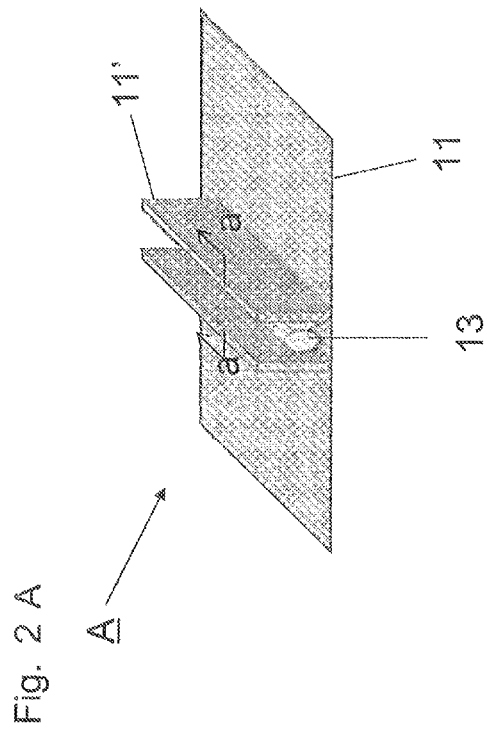
FIG. 2A is a schematic diagram showing an embodiment of the culturing device of the present invention for hepatocytes (lateral view).
FIG. 2B is a schematic diagram showing an embodiment of the culturing device of the present invention for hepatocytes (cross-sectional view taken along the a-a line).
Figure 2:
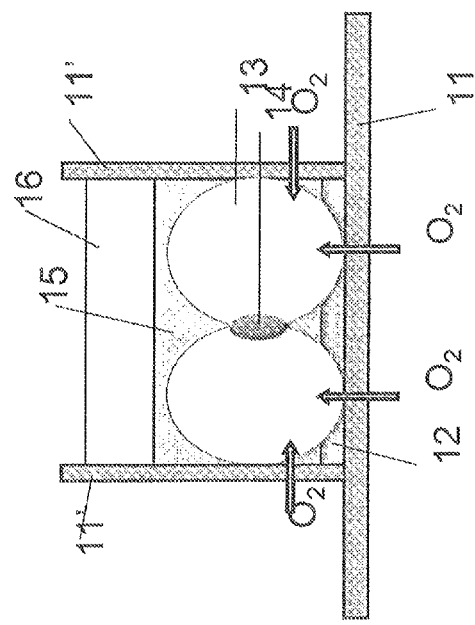

The high-throughput screening is possible by constructing a micropassage device having very small compartments separated from each other or having ultrafine passages each of which may be a gas-permeable passage such as the one shown in FIG. 2, which compartments or passages contain cultured hepatocytes that are embedded in an extracellular matrix and forming bile canaliculi, which micropassage device has, in each compartment, an inlet for exposure of a test compound and an opening for collection of a metabolite that has been metabolized by the hepatocytes and excreted into the bile canaliculi.

For example, the inlet of the micropassage device is connected to a pump for collecting and sending a compound solution from a compound library, and the outlet is connected to a passage through which the metabolite is sent to a high-performance liquid chromatography or LC/MS/MS to obtain results of quantification or composition analysis of the metabolite, which pump and passage may be operated by a computer or the like.

The present invention will now be described in more detail by way of Examples below, but the present invention is not restricted by these Examples.

EXAMPLE 1

Culture of Hepatocytes by Method of Present Invention and Confirmation of Formation of Bile Canaliculus Isolation of Hepatocytes From the liver of rats of 5 weeks old (purchased from Sankyo Labo Service Corporation), cells derived from the liver were separated according to a Non-patent Document (Seglen P O, 1976, in Methods in cell biology (Prescott D M ed) 13th ed, pp 29-83, Academic press, New York).

Preparation of 24-well Culturing Device Having PDMS Membrane to Which Collagen is Covalently Bound The method was carried out according to the method described in a Non-patent Document (M. Nishikawa et al. Biotechnology and Bioengineering, 2008, vol. 99, pp. 1472-1481). The base compound and the curing agent of Silpot 184 (manufactured by Dow Corning Toray Co., Ltd.) were mixed together at a ratio of 10:2 to prepare a mixture, and 30 g of this mixture was thinly spread on a plastic container having a size of 258 mm×174 mm×45 mm, followed by curing the mixture at 80° C. for 2 hours to prepare a PDMS membrane having a thickness of 1 mm. The ratio between the base compound and the curing agent is not restricted to 10:2, and the ratio is usually 10:1 to 10:2 in the preparation. The PDMS membrane was sandwiched between a polycarbonate frame having 24 holes and an SUS plate having a thickness of 1.5 mm having holes at the same positions as those on the frame, and the frame and plate were immobilized with screws, to prepare a PDMS membrane 24-well culturing device. The device was subjected to oxygen plasma treatment (for 5 seconds), and 1% acetic acid, 2% aminosilane (manufactured by Shin-Etsu Silicone) was added to each well to allow reaction to proceed at room temperature for 45 minutes, followed by heating of the reaction solution at 80° C. for 90 minutes. Subsequently, a 0.5 mM sulfosuccinimidyl 2-(m-azido-o-nitrobenzamido)-ethyl-1,3'-dithiopropionate solution (manufactured by Thermo Fisher Scientific) was added to the thus treated wells, and UV irradiation was carried out (2 times of 1-minute irradiation), followed by addition of a 0.3 mg/mL collagen solution (manufactured by Nitta Gelatin Inc.) to the wells, leaving the resulting mixture for 18 hours at room temperature and washing the resultant with PBS. The prepared device was used on the same day in the following experiment.

Culture of Hepatocytes by Collagen Gel Sandwich Method and Confirmation of Formation of Bile Canaliculi The collagen gel sandwich method was carried out according to Non-patent Document 1 (LeCluyse et al., Am J Physiol, 1994, vol. 266, pp. 1764-1774). Hepatic parenchymal cells were plated on the above prepared culturing device at $2 \times 10^5$ cells/well, and the culture medium was replaced 4 hours later. Twenty four hours after the plating, 20 μL of a 1.7 mg/ml collagen solution (manufactured by Becton, Dickinson and Company) was deposited on the cells, and gelation was allowed to proceed at 37° C. for 1 hour, followed by adding 500 μL of a serum-free medium and culturing the cells at 37° C. at 5% $CO_2$. The culture medium was replaced once every 2 days.

Figure 5:
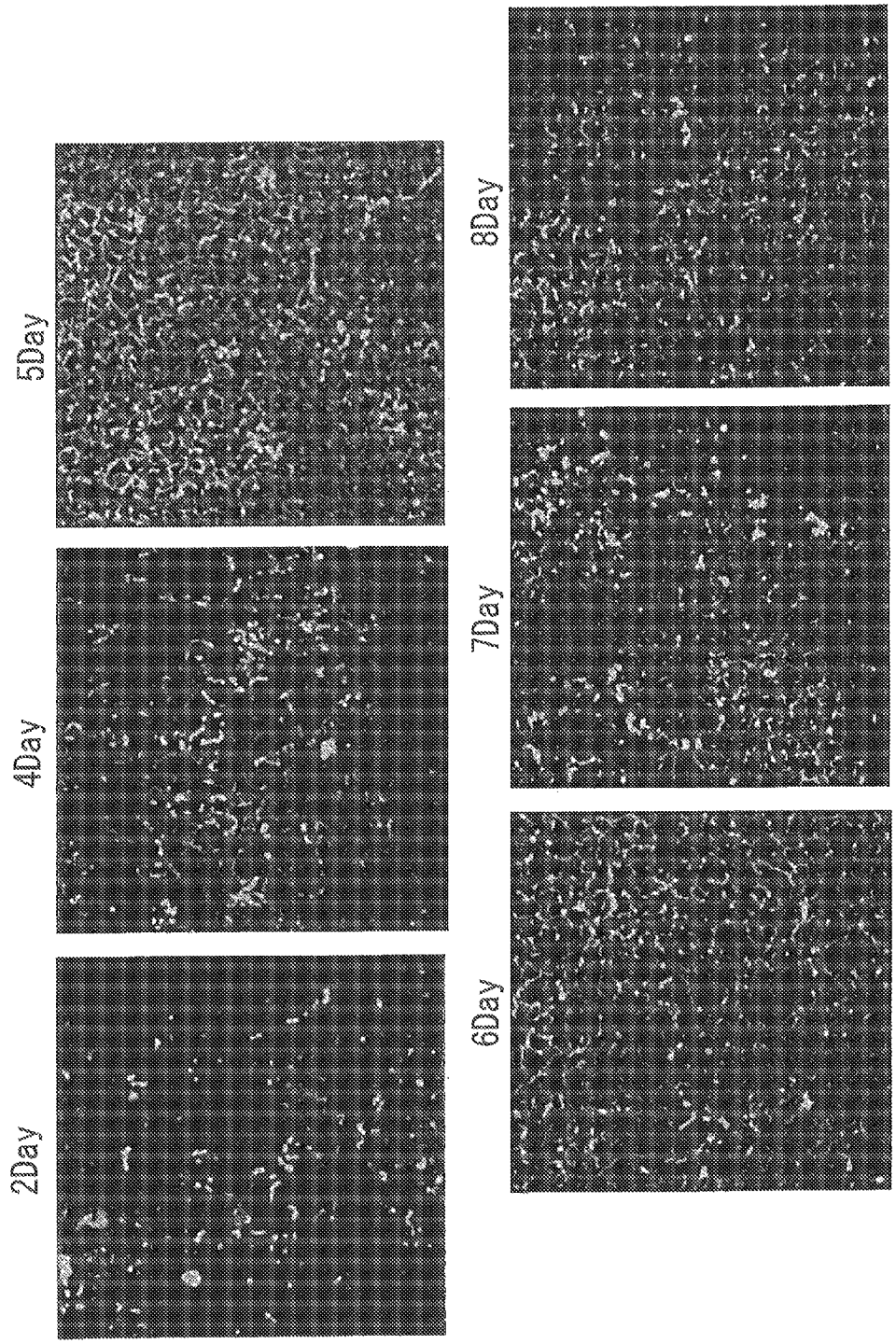
FIG. 5 is a diagram (photographs) showing the metabolism of 5-(and-6)-carboxy-2',7'-dichlorofluorescein (CDCF) in hepatocytes cultured in a culturing device having a PDMS membrane.

Hepatic cells have a property that, when 5-(and-6)-carboxy-2',7'-dichlorofluorescein (CDCF) was administered, they incorporate this substance into the cytoplasm and metabolize the substance to convert the substance to a fluorescent substance fluorescein, followed by excreting the fluorescein to into a bile canaliculus. Using this property, the process of formation of bile canaliculi and the area of the bile canaliculi were investigated. Fluorescein diacetate was added to the culture medium at a concentration of 5 μM, and the resulting mixture was left to stand at 37° C. for 15 minutes followed by washing the cells with a cooled culture medium. Fluorescence of the fluorescein was observed under the microscope-equipped with a fluorescence observing device. As shown in FIG. 5, the hepatocytes cultured on the PDMS membrane began to be stained on Day 2 with the fluorescent dye at their tubular structures. This indicates that bile canaliculi were formed.

Figure 6:
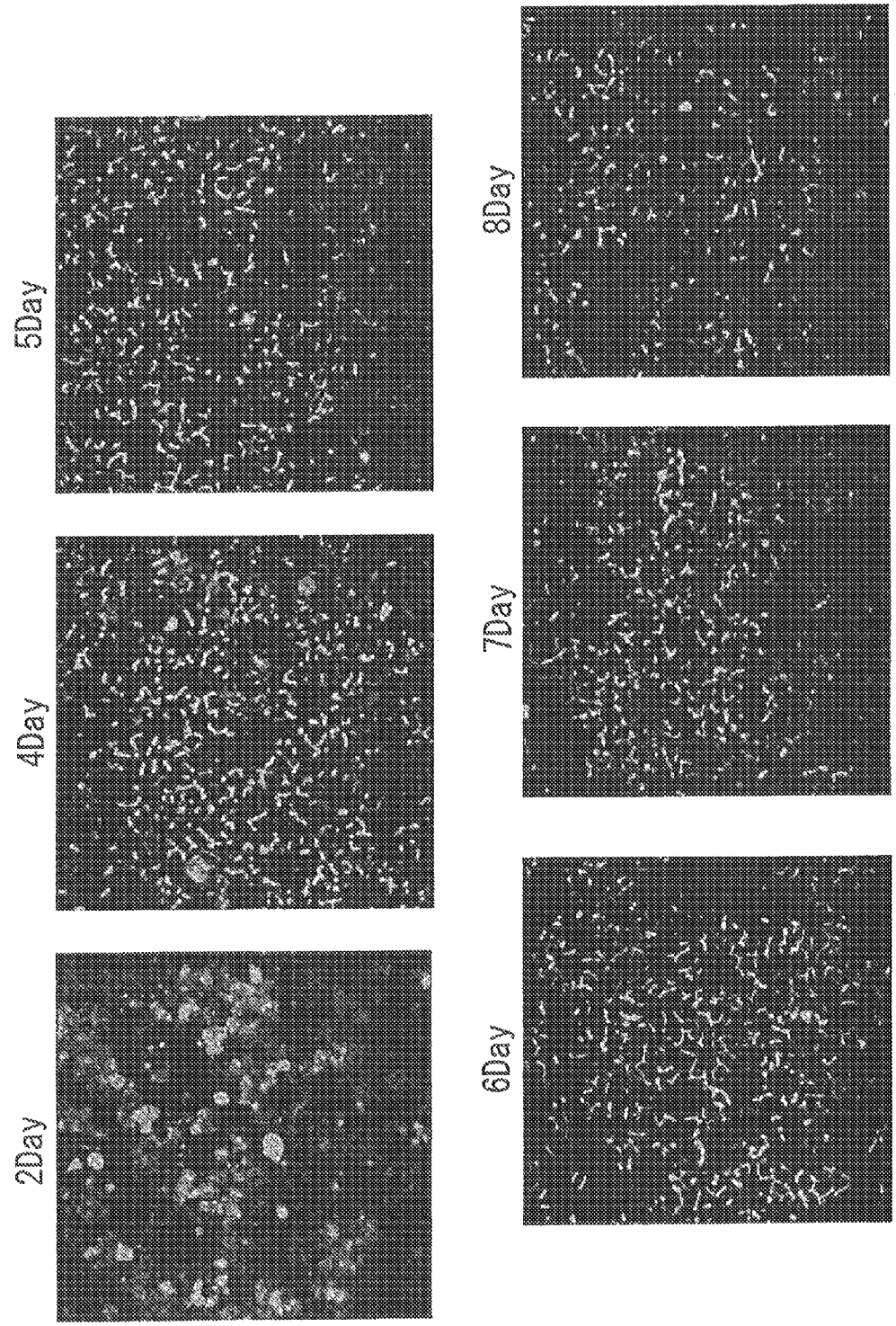
FIG. 6 is a diagram (photographs) showing the metabolism of 5-(and-6)-carboxy-2',7'-dichlorofluorescein (CDCF) in hepatocytes cultured in a culturing device having a polystyrene culturing device.

On the other hand, as shown in FIG. 6, the hepatocytes cultured on a conventional polystyrene culturing device (trade name, BioCoat Collagen I-coated 24-well; manufactured by Becton, Dickinson and Company) hardly showed tubular structures on Day 2, and, since the cells did not have the excretion activity, most of the cells were stained in their inside.

Figure 7:
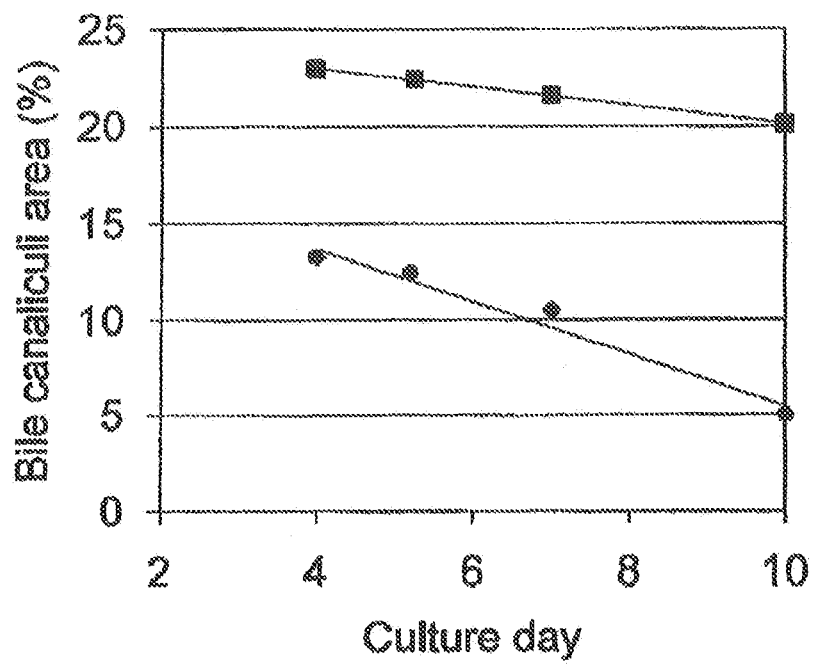
FIG. 7 is a graph showing changes in the area of bile canaliculi with time. ■ represents a culturing device having a PDMS membrane, and ● represents a polystyrene culturing device.

Comparison of the area of bile canaliculi with time showed that, from Day 2 to Day 10, the area of formation of bile canaliculi was larger in the case of culture on the PDMS membrane than in the case of culture on the conventional polystyrene. On the other hand, in the case of culture on the conventional polystyrene, bile canaliculi gradually decreased with time, while in the case of culture on the PDMS membrane, remarkable decrease in bile canaliculi was not observed (FIG. 7).

From these results, it was revealed that preparation of hepatocytes efficiently and stably forming bile canaliculi for a long period is possible by culturing the cells on a PDMS membrane.

EXAMPLE 2

Study of Method of Pretreatment of PDMS Membrane

A comparison was made between the culturing device having a PDMS membrane to which collagen is covalently bound, which was prepared in Example 1, and a culturing device having a PDMS membrane to which collagen was bound by adsorption, in terms of the efficiency to form bile canaliculi.

Preparation of PDMS Membrane 24-well Culturing Device

A 24-well culturing device having a PDMS membrane to which collagen is covalently bound was prepared in the same manner as in Example 1. A 24-well culturing device having a PDMS membrane to which collagen was bound by adsorption was prepared by adding a small quantity of a 1.7 mg/mL collagen solution (manufactured by Becton, Dickinson and Company) to each well of the PDMS membrane 24-well culturing device subjected to the aminosilane treatment step and then to the oxygen plasma treatment in Example 1, to cover the well, and leaving the resultant to stand for 18 hours at room temperature, followed by washing the resultant with PBS. Both of these devices were used on the same day in the following experiment.

Preparation of Collagen Gel Sandwich and Visualization of Bile Canaliculi

Figure 8:
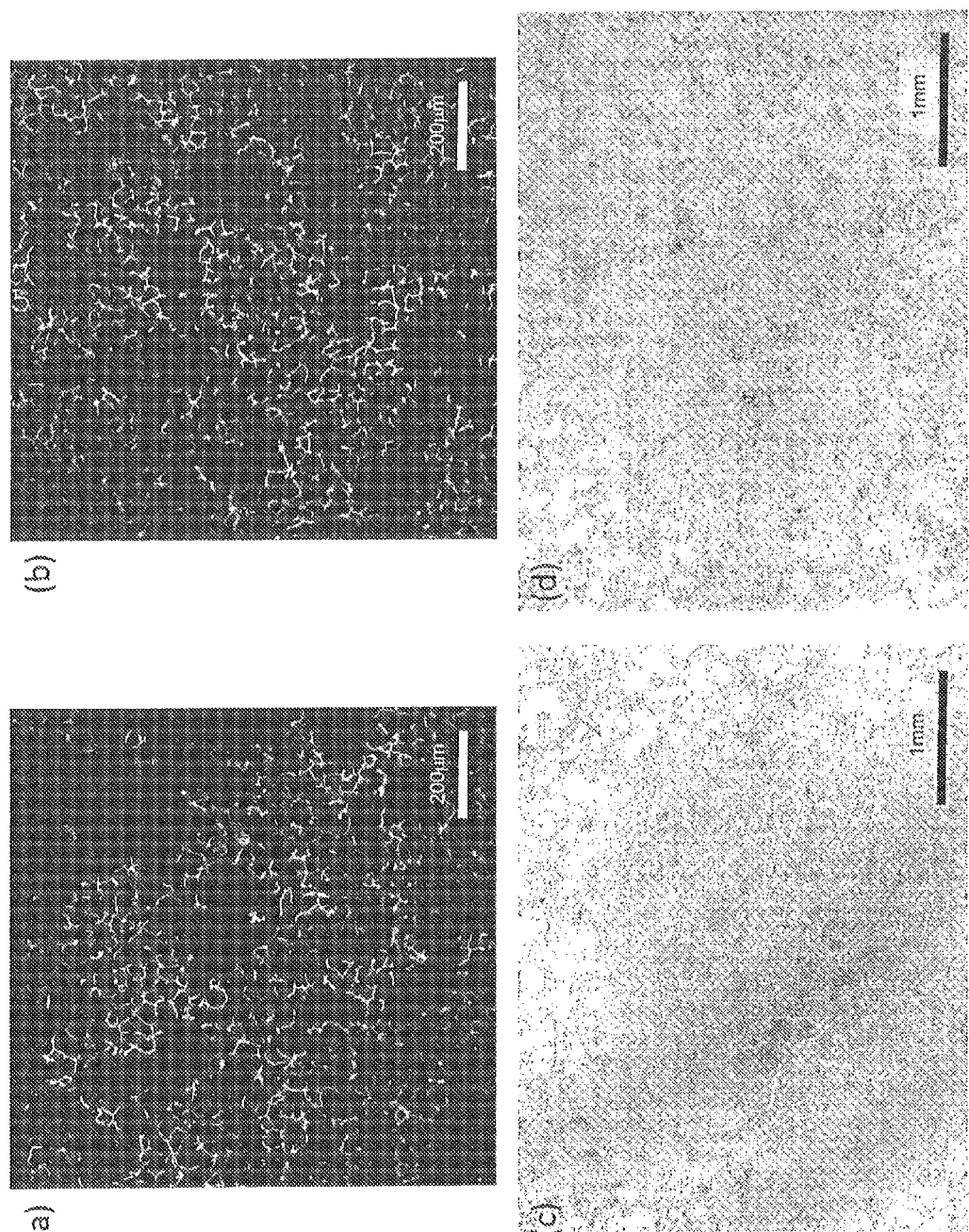
FIG. 8 is a diagram (photographs) showing results of observation of formation of bile canaliculi using fluorescein diacetate. (a) and (c) show results obtained with a culturing device to which collagen is bound by adsorption, wherein (a) shows a photograph taken on Day 4 of culture, and (c) shows a photograph taken on Day 7 of culture; (b) and (d) show results obtained with a culturing device to which collagen was covalently bound, wherein (b) shows a photograph taken on Day 4 of culture, and (d) shows a photograph taken on Day 7 of culture.

In the same manner as in Example 1, a collagen gel sandwich hepatocyte culture was prepared. When formation of bile canaliculi was studied using fluorescein diacetate (FIG. 8), formation of bile canaliculi was found on Day 4 of the culture (3 days after deposition of the collagen gel) both for the culturing device to which collagen was bound by adsorption (a) and for the culturing device to which collagen was covalently bound (b). However, on Day 7 of culture, detachment of the cells was more remarkable in the culturing device to which collagen was bound by adsorption (c), as compared to the culturing device to which collagen was covalently bound (d), and the bile canaliculi have disappeared in the former case.

Thus, by covalently binding collagen, preparation of hepatocytes forming bile canaliculi more stably for a longer period is possible.

EXAMPLE 3

Study of Extracellular Matrix Component to be Deposited

In the culturing device having a PDMS membrane to which collagen is covalently bound, which was prepared in Example 1, the efficiency of formation of bile canaliculi was compared among extracellular matrices to be deposited.

This study was carried out in the same manner as in Example 1 except for the extracellular matrix component to be deposited. On the culturing device prepared as described above, $2 \times 10^5$ cells/well of hepatic parenchymal cells were seeded, and the culture medium was replaced 4 hours later. Twenty four hours after the plating, 20 μL of a 1.7 mg/ml collagen solution (manufactured by Becton, Dickinson and Company) was deposited on the cells, and gelation was allowed to proceed at 37° C. for 1 hour, to provide a collagen gel sandwich group. On the other hand, 24 hours after the plating, Matrigel (manufactured by Becton, Dickinson and Company) 50-fold diluted (corresponds to a concentration of 150 μg/mL) with a serum-free medium was added to the cells to provide a Matrigel sandwich group. Cells to which none of these was added were provided as an untreated group.

Figure 9:
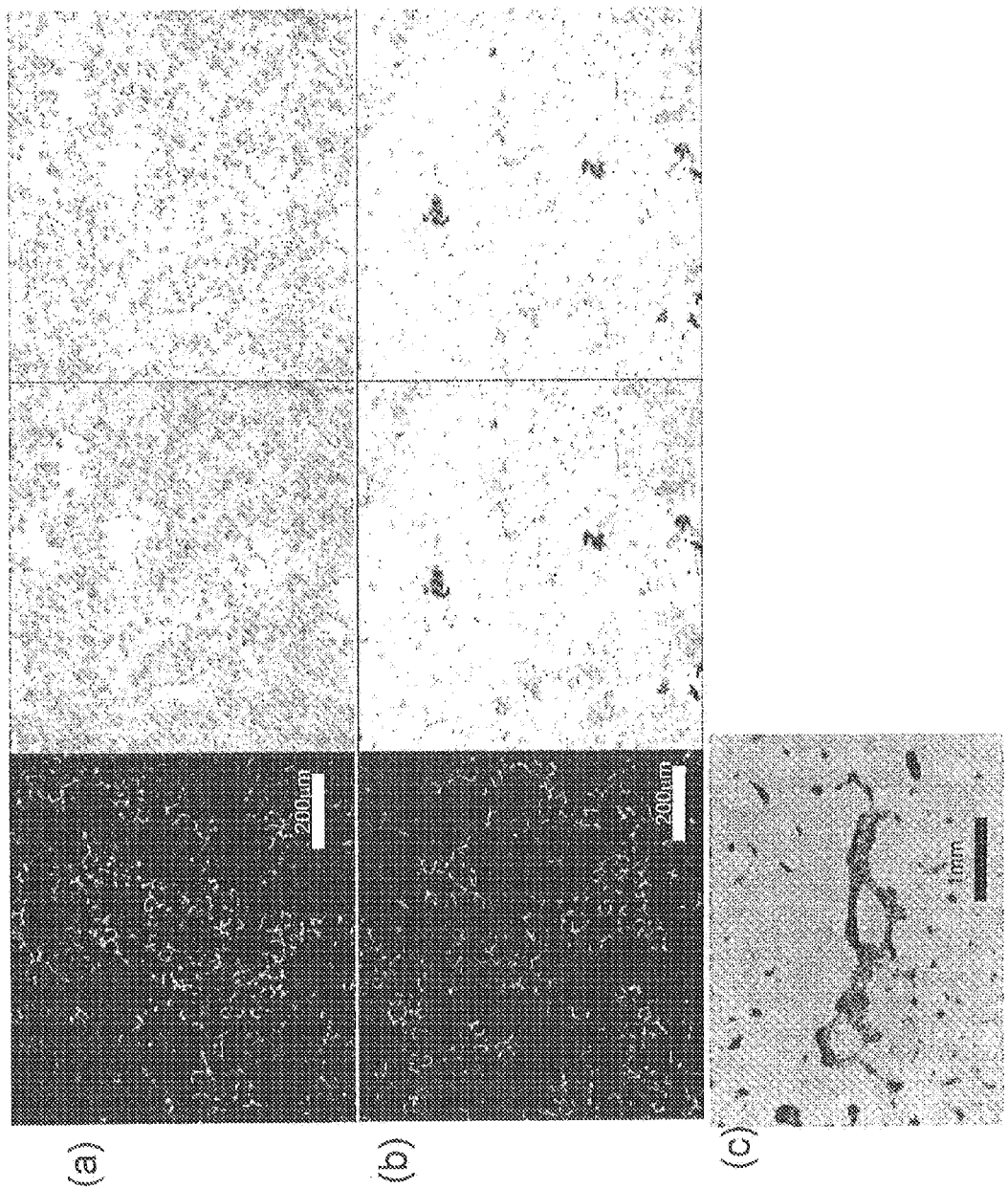
FIG. 9 is a diagram (photographs) showing results of observation of formation of bile canaliculi using fluorescein diacetate. (a) shows results for the collagen gel sandwich group; (b) shows results for the Matrigel sandwich group; and (c) shows a result for the untreated group.

When formation of bile canaliculi was studied using fluorescein diacetate (FIG. 9), formation of bile canaliculi was found on Day 4 of the culture (3 days after deposition of the extracellular matrix component) both for the collagen gel sandwich group (a) and for the Matrigel sandwich group (b), which bile canaliculi were maintained until Day 7 of the culture. In the untreated group, no bile canaliculus was formed at all, and remarkable detachment of the cells was observed from Day 3 of the culture, and most of the cells were detached by Day 5 (c).

From these results, it was revealed that bile canaliculi can be formed on a PDMS membrane either by deposition of collagen or by deposition of Matrigel.

EXAMPLE 4

Measurement of MRP2 Activity with 5-(and-6)-carboxy-2',7'-dichlorofluorescein (CDCF)

Using the collagen gel sandwiched hepatocytes that were cultured on the PDMS membrane culturing device prepared in Example 1 and forming bile canaliculi, the activity of a drug transporter (MRP2) was measured by incorporation of 5-(and-6)-carboxy-2',7'-dichlorofluorescein (CDCF) as follows according to a Non-patent Document (Liu X et al., Am J Physiol, 1999, vol. 277, pp. 12-21). Further, hepatocytes cultured in a conventional polystyrene culturing device were used for comparison.

Materials

Ca/Mg(+) HBSS was prepared before use by mixing 50 mL of HBSS (Invitrogen, 14175-079), 500 μL of 14 g/L $CaCl_2$ and 500 μL of 10 g/L $MgCl_2/6H_2O$ together. In terms of the CDCF solution, a 5 μM CDCF solution was prepared before use by using 1 mM CDCF (in dimethyl sulfoxide: Molecular Probes, C-369) and Ca/Mg(+) HBSS, and the prepared solution was incubated in a water bath at 37° C. Ca/Mg(−) HBSS was prepared by adding 500 μL of 100 mM EGTA to 50 mL of HBSS (Invitrogen, 14175-079). Further, 0.5% Triton X-100/PBS was prepared by adding Triton X-100 to PBS buffer at a concentration of 0.5%.

Application and Collection of Compound (in Case of 24-well Plate)

Two hepatocyte cultures were prepared 4 days after the beginning of the culture (3 days after the deposition of the gel). Subsequently, each culture was separately washed twice with 0.5 mL of warm Ca/Mg(+) HBSS or warm Ca/Mg(−) HBSS buffer. Thereafter, each culture was separately left to stand in 0.5 mL of warm Ca/Mg(+) HBSS or warm Ca/Mg(−) HBSS buffer at 37° C. for 10 minutes, and the liquid was then removed. Subsequently, 0.5 mL of warm Ca/Mg(+) HBSS buffer supplemented with 5 μM CDCF was added to the both cultures, and the resultants were incubated for 5 minutes, followed by removal of the CDCF solution. This was followed by 3 times of washing of the both cultures with 0.5 mL of cold Ca/Mg(+) HBSS buffer, and removal of the liquid. Thereafter, 500 μL of PBS supplemented with 0.5% Triton X-100 was added to each culture and the resultant was left to stand at room temperature for 20 minutes to allow permeation, followed by collecting the liquid, centrifuging the collected liquid at 13000×g for 15 minutes at 4° C. and collecting the supernatant. A 100-μL aliquot was collected from each supernatant and subjected to measurement with a fluorescence microplate reader with excitation at 492 nm and fluorescence at 530 nm to quantify the amount of CDCF. Further, 25 μL of the undiluted solution was subjected to measurement of the protein amount using BCA Protein Assay Kit (manufactured by Thermo). The Bile Excretion Index (BEI) was calculated according to the following equation based on the fluorescent brightness per protein amount (Accumulation).

$$BEI = \frac{\text{Accumulation}(Ca^{2+}/Mg^{2+}(+)) - \text{Accumulation}(Ca^{2+}/Mg^{2+}(-))}{\text{Accumulation}(Ca^{2+}/Mg^{2+}(+))} \cdot 100$$

Figure 10:
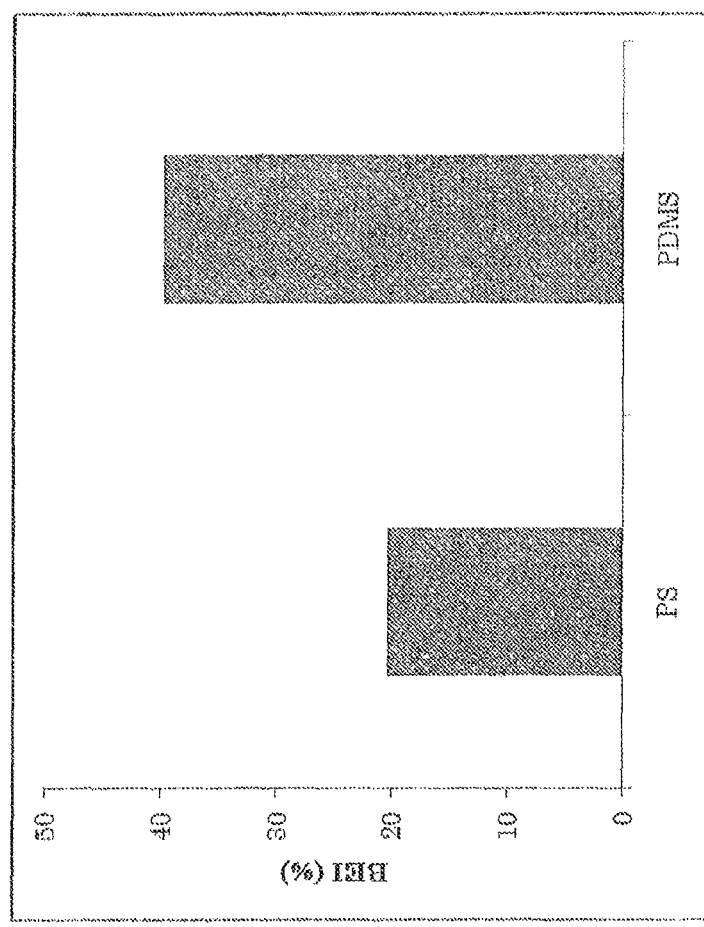
FIG. 10 shows comparison of BEI (bile excretion index) after 5 minutes of bile excretion reaction between polystyrene (PS) and a PDMS membrane.

The results are shown in FIG. 10. In the case where the gas-permeable membrane was used, the BEI value was about 40%, while in the case where the polystyrene (PS) substrate was used, the BEI value was about 20%.

From the above results, it was revealed that use of a gas-permeable membrane enables hepatocytes to form a bile canaliculus structure having a higher MRP excretion activity as compared to use of a polystyrene substrate, and hence allows a highly sensitive evaluation of a compound (that is, accurate evaluation of a small amount of a compound).

EXAMPLE 5

Analysis of Localization of MRP2 Protein

Using hepatocytes that were cultured on the PDMS membrane culturing device prepared in Example 1 and forming bile canaliculi, localization of the MRP2 protein was investigated according to a conventional method by cell antibody staining. Further, hepatocytes cultured in a conventional polystyrene culturing device were used for comparison.

Although the MRP2 protein was detected between cells in both the PDMS culturing device and the conventional polystyrene culturing device, expression of the MRP2 protein was observed in a broader area in the PDMS culturing device (FIG. 11). Since MRP2 is a major transporter involved in excretion of bile, it can be assumed that the bile canaliculi prepared with the PDMS culturing device have a higher bile excretion activity.

EXAMPLE 6

Study of Early-phase Polarity Formation by PDMS Membrane to Which Collagen was Bound by Adsorption, and Matrigel In the 24-well culturing device having a PDMS membrane to which collagen was bound by adsorption, which was prepared in Example 2, and a collagen-coated polystyrene 24-well plate (Beckton Dickinson), hepatocytes prepared from rats were seeded. The culture medium was replaced, 2 hours after the seeding, with William's Medium E (containing 5 μg/mL insulin, 5 μg/mL transferrin, 5 μg/mL selenious acid and 1 μM dexamethasone) supplemented with Matrigel.

Figure 12:
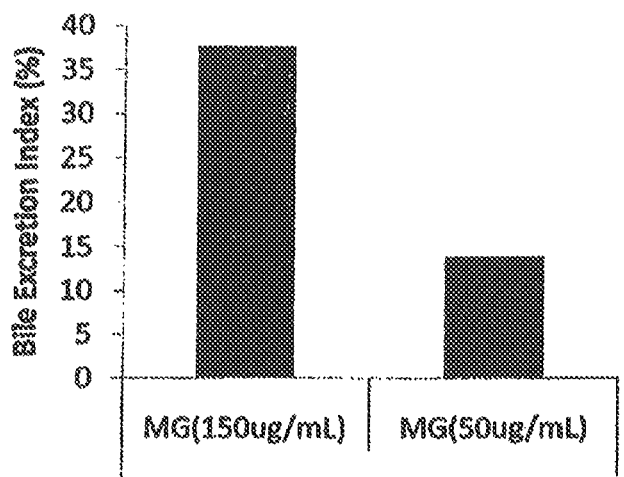
FIG. 12 shows comparison of BEI between Matrigel (MG) concentrations of 150 μg/mL and 50 μg/mL.

To study the concentration of Matrigel (MG), 2'10$^5$ cells/well of the hepatocytes were seeded on the 24-well culturing device having a PDMS membrane to which collagen was bound by adsorption, and, when the culture medium was replaced 2 hours after the seeding, the concentration of Matrigel in the culture medium was set to 50 and 150 μg/mL. After 48 hours of culture, BEI was measured according to the method described in Example 4. As a result, as shown in FIG. 12, a higher BEI was observed in the case of 150 μg/mL Matrigel than in the case of 50 μg/mL Matrigel.

Figure 13:
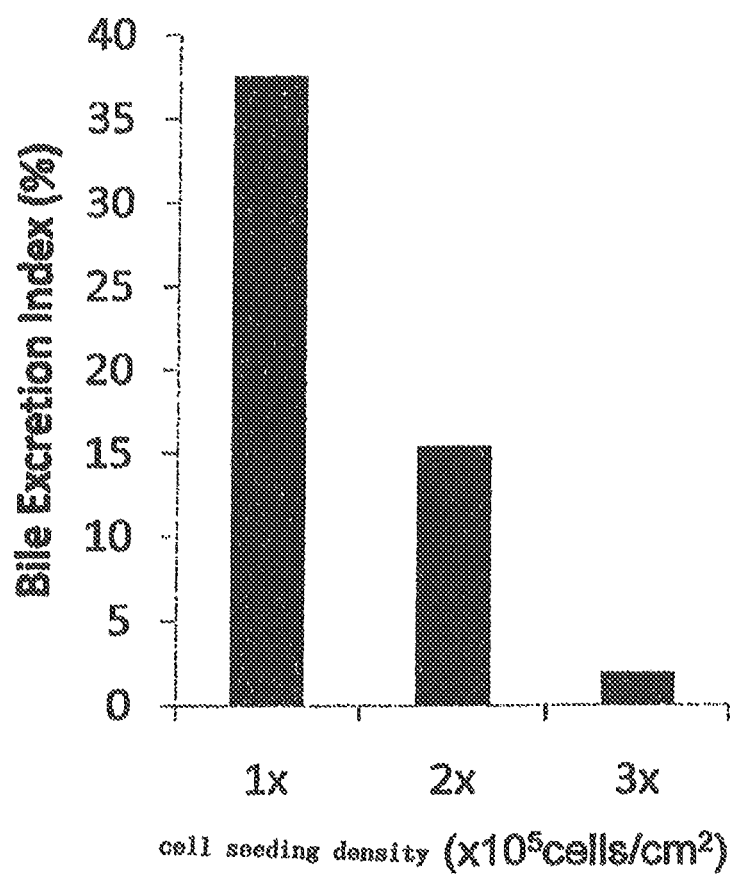
FIG. 13 shows comparison of BEI among seeding densities of hepatocytes of $2\times10^5$ cells/well, $4\times10^5$ cells/well and $6\times10^5$ cells/well.

Further, in order to study the plating density of the cells, the hepatocytes were plated on the 24-well culturing device having a PDMS membrane to which collagen was bound by adsorption at plating densities of $2\times10^5$, $4\times10^5$ and $6\times10^5$ per well, and cultured for 48 hours with 150 μg/mL Matrigel, followed by measuring BEI according to the method described in Example 4. As a result, as shown in FIG. 13, the highest BEI was observed at the plating density of $2\times10^5$, followed by the plating densities of $4\times10^5$ and $6\times10^5$ in that order.

Subsequently, the optimum point of the culture period was studied. At the thus determined Matrigel concentration (150 μg/mL) and the cell plating density ($2\times10^5$ cells), BEI measurement was carried out 24, 48, 72 and 96 hours after the seeding of hepatocytes according to the method described in Example 4.

Figure 14B:
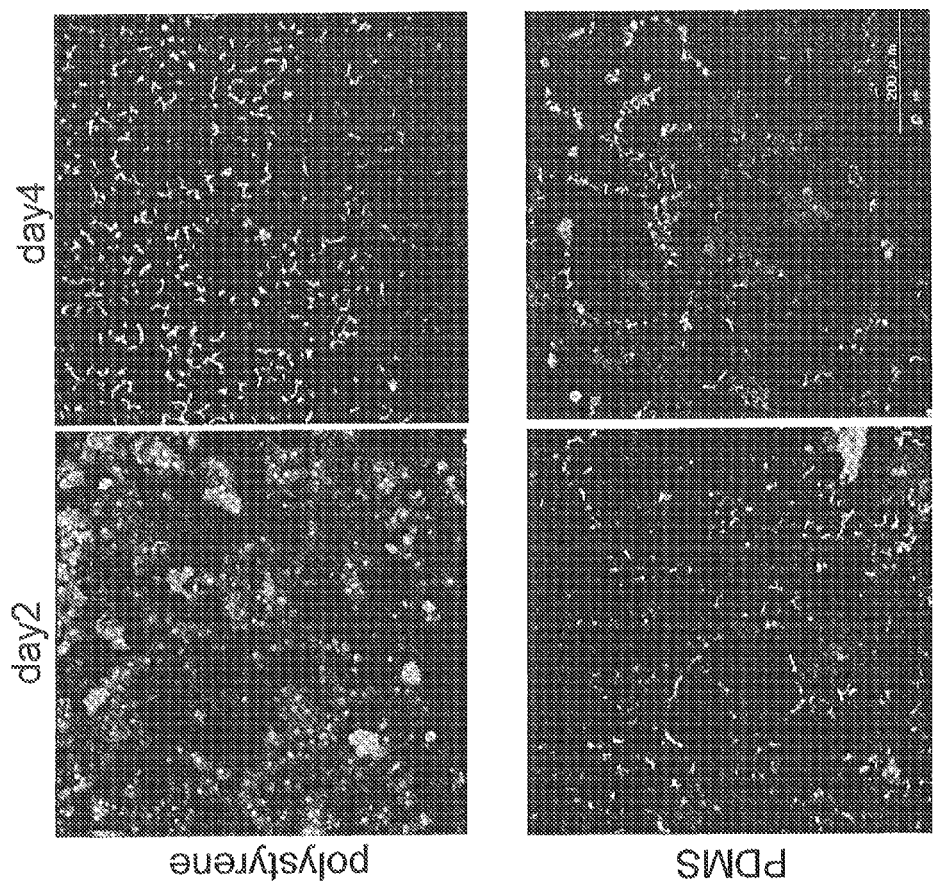
FIG. 14B shows fluorescence micrographs of cells in a culturing device having a PDMS membrane to which collagen is bound by adsorption and in a collagen-coated polystyrene plate, which fluorescence micrographs were taken after 2 days and 4 days of culture.

As shown in FIG. 14A, BEI observed for the PDMS membrane 24 and 48 hours after the seeding was equivalent to BEI observed when hepatocytes were cultured on polystyrene for 96 hours. FIG. 14B shows fluorescence micrographs of portions where CDCF accumulated, which micrographs were taken 48 hours and 96 hours after the seeding of hepatocytes on the PDMS membrane 24-well culturing device and on the collagen-coated polystyrene 24-well plate. It can be confirmed also from these images that formation of active bile canaliculi occurred earlier in hepatocytes on the PDMS membrane than in hepatocytes cultured by the conventional method. Based on these results, when a PDMS membrane 24-well culturing device was used and Matrigel was deposited to induce the polarity, the polarity was formed by 24 hours after the plating, leading to appearance of functional bile canaliculi. It was proved that this occurs 72 hours earlier than achievement of an equivalent BEI value by a conventional method.

EXAMPLE 7

Demonstration of Localization/Expression of Polarity Marker

Using the hepatocytes forming bile canaliculi, which were prepared in Example 6, localization of MRP2 and a basement membrane marker CD147 were investigated according to a conventional method by cell antibody staining. Further, the results were compared with those obtained with hepatocytes cultured on a collagen-coated polystyrene 24-well plate.

Figure 15:
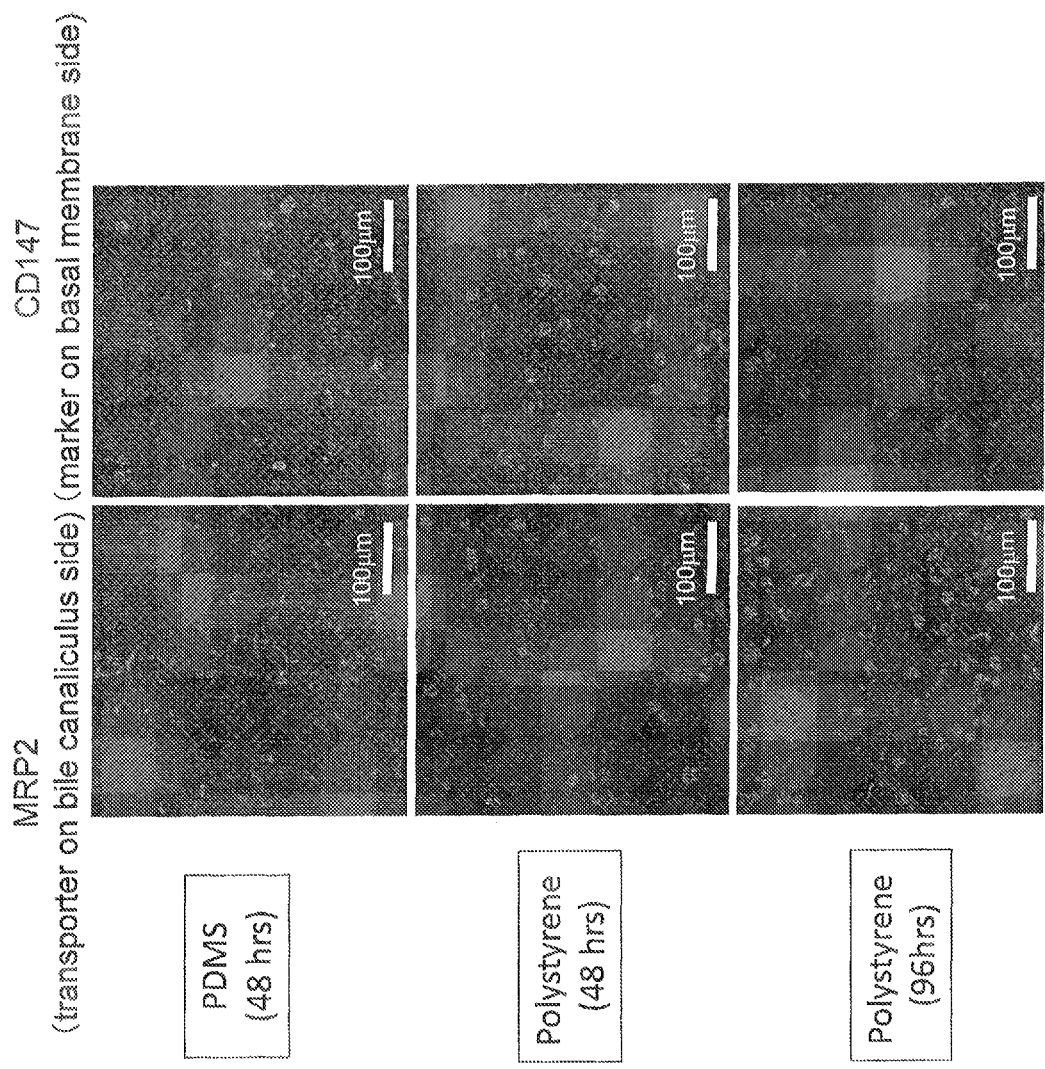
FIG. 15 shows fluorescence micrographs showing localization of MRP2 and CD147 in a culturing device having a PDMS membrane to which collagen is bound by adsorption (48 hours) and in a collagen-coated polystyrene plate (48 hours and 96 hours).

As shown in FIG. 15, when the cells were cultured on the PDMS membrane, the MRP2 protein and the CD147 protein were detected between the cells after 48 hours of culture. On the other hand, on the conventional polystyrene, expression of CD147 was observed, but localization of the MRP2 protein was hardly observed. The area of expression of the MRP2 protein was broader in hepatocytes on the PDMS membrane even in comparison with that in the cells already having the polarity on polystyrene after 120 hours of culture. The localization pattern of CD147 was almost the same between the both. From these results, it was shown that hepatocytes cultured on a PDMS membrane cause localization of MRP2 molecules earlier than hepatocytes cultured on polystyrene, and the expression level of MRP2 is higher in the case of a PDMS membrane than in the case of polystyrene.

EXAMPLE 8

Demonstration of Polarity Formation by Observation of Ultrafine Structure

The ultrafine structure of the hepatocytes after 48 hours of culture, which were prepared in Example 6, was observed with a transmission electron microscope (JEM1400, manufactured by JEOL).

Figure 16:
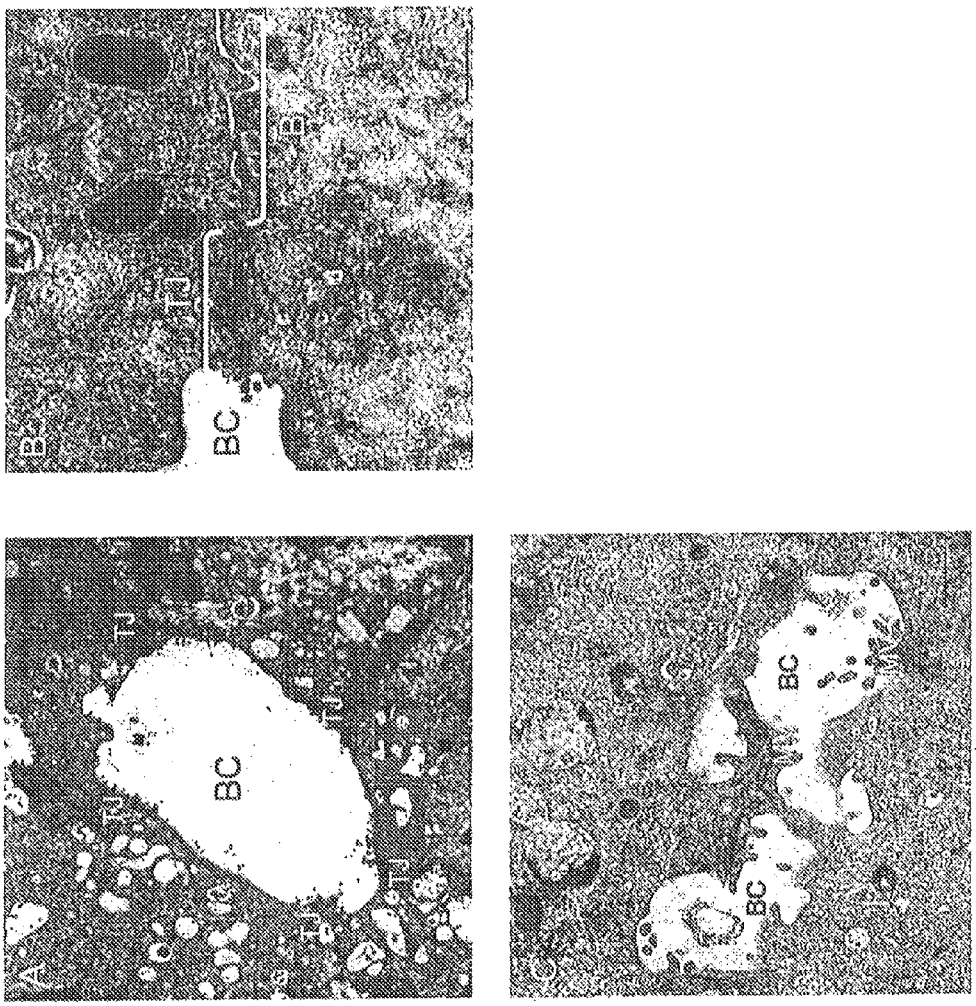
FIG. 16 shows (A) electron micrographs of hepatocytes cultured on a PDMS membrane. (B) shows a magnified photograph showing a portion having tight junctions. (C) shows a picture of bile canaliculi having microvilli (MV) on the walls of the cavities. The scale bars represent 2 μm in (A) and (C), and 1 μm in (B).

As shown in FIG. 16A, in the hepatocytes whose polarity was induced on a PDMS membrane, bile canaliculus cavities (BC) and tight junctions (TJ), which are typically observed in hepatocytes having a polarity, were observed. FIG. 16B shows a magnified photograph showing a portion having tight junctions, and FIG. 16C shows bile canaliculi having microvilli (MV) on the wall of the cavities.

From these results, it was shown that, in hepatocytes cultured by the present method, a polarity which is structurally equivalent to that in a living body is formed.

EXAMPLE 9

Study of Early-stage Formation of Polarity in Hepatocytes on Gas-permeable Plate Using Fluorocarbon Membrane Hepatocytes prepared from rats were seeded on a 24-well culture plate Lumox (manufactured by In vitro systems and services), which has a culturing area where a gas-permeable fluorocarbon membrane is placed, at a density of $1.0 \times 10^5$ cells or $2.0 \times 10^5$ cells per well. The culture medium was replaced, 2 hours after the seeding, with William's Medium E (containing 5 µg/mL insulin, 5 µg/mL transferrin, 5 µg/mL selenious acid and 1 µM dexamethasone) supplemented with 150 µg/mL Matrigel. BEI was measured 48 hours after the seeding of hepatocytes, according to the method described in Example 4, to analyze the extent of polarity formation. As a control for comparison, cells cultured on a collagen-coated polystyrene 24-well plate were used.

As shown in FIG. 17, a higher BEI was observed for Lumox as compared to the polystyrene (PS) 24-well plate. A higher BEI was given at the cell plating density of $1.0 \times 10^5$ than at the plating density of $2.0 \times 10^5$.

EXAMPLE 10

Preparation of Continuous Bile Canaliculus for Continuous Analysis of Metabolite To a fluorocarbon membrane prepared in the same manner as described in Example 1, 0.001 N HCl solution supplemented with 100 µg/mL collagen I-P (manufactured by Nitta Gelatin Inc.) was applied, and the solution was then dried, to perform collagen coating treatment.

Subsequently, hepatocytes were regularly arranged on the above prepared substrate. As shown in FIG. 18A, a PDMS mold having a protruded portion having a width of 30 µm, height of 100 µm and length of 10 mm was placed on a collagen solution (at a concentration of 2.1 mg/mL) before gelation, and left to stand at 37° C. for 60 minutes to allow gelation, to prepare a collagen gel having a recess.

Thereafter, as shown in FIG. 18B, rat hepatocytes suspended in a culture medium were plated on the gel having the prepared recess, and the cells were washed twice with the culture medium, to arrange the hepatocytes only in the recess, followed by culture of the cells.

Figure 19:
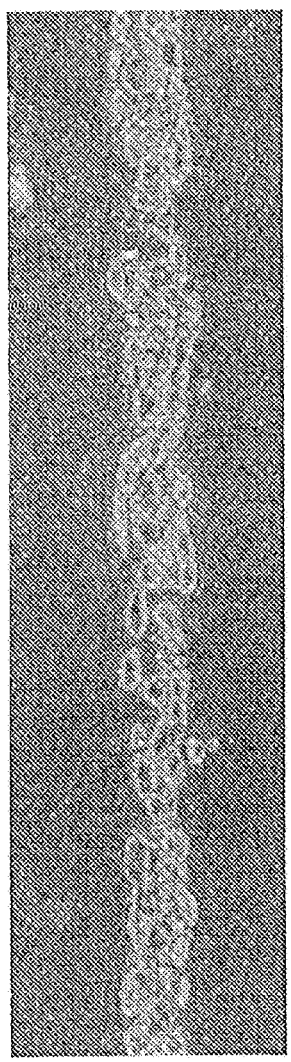
FIG. 19 is a micrograph of hepatocytes cultured in the recess.

Twenty four hours later, a collagen solution (at a concentration of 2.1 mg/mL) was deposited on the cells, and additional culture was then carried out for 9 days. A photograph of the thus arranged hepatocytes on Day 9 is shown in FIG. 19. It appeared that the cells were forming continuous bile canaliculi.

Figure 20:
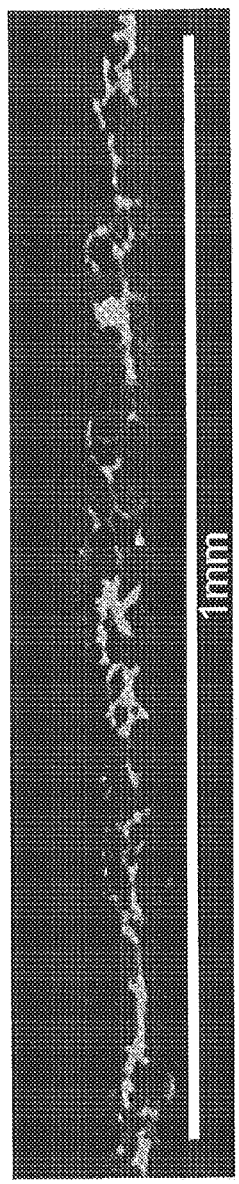
FIG. 20 is a diagram (photograph) showing the metabolism of CDCF in a continuous bile canaliculus.

Subsequently, in order to confirm that the above-described bile canaliculi formed are actually continuous, CDCF was added to the culture medium in the same manner as described in Example 1 to allow accumulation of fluorescein as a metabolite in the above prepared continuous bile canaliculi, and fluorescence from the fluorescein was observed. On Day 2, formation of bile canaliculi could be observed in a part of the cells, and, on Day 6, it could be observed that those bile canaliculi were continuous. On Day 9, it could be observed that the bile canaliculi continued even longer. A result obtained on Day 9 is shown in FIG. 20. Since continuous fluorescence was observed, it could be confirmed that a continuous bile canaliculus having a length of not less than 1 mm can be prepared.

Figure 21:
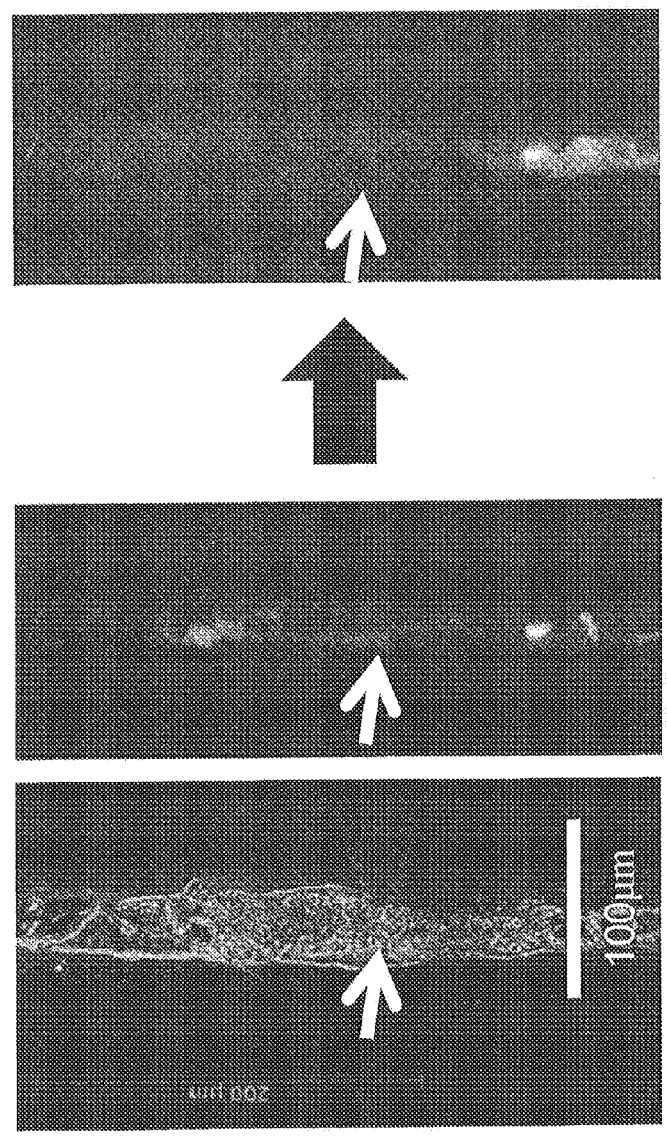
FIG. 21 is a diagram (photographs) showing results of an experiment wherein the metabolism of CDCF was allowed to occur in a continuous bile canaliculus to cause accumulation of fluorescein, followed by opening one end of the bile canaliculus using a thin glass tube. A shows a bright-field image of the tissue, and B and C show fluorescent images obtained before the opening and about 60 seconds after the opening, respectively. The white arrows indicate the position of the opening.

Further, fluorescein was allowed to accumulate in a prepared continuous bile canaliculus, and one end of the bile canaliculus (FIG. 21A) was opened with a thin glass tube. As a result, it was revealed that fluorescein that had accumulated in the bile canaliculus before the opening (FIG. 21B) disappeared about 60 seconds after the opening (FIG. 21C). By this, the continuity of the bile canaliculus could be demonstrated, and possible use of the bile canaliculus for analysis of bile acid by continuous collection was also demonstrated. Further, in the above experiment, the 2 0 results were not influenced by whether or not the collagen coating treatment of the fluorocarbon oxygen-permeable membrane was carried out.

INDUSTRIAL APPLICABILITY

Cultured hepatocytes obtained by the culture method of the present invention can be used for, for example, an assay using hepatocytes for screening of a candidate compound for a pharmaceutical agent. The method contributes to improvement of the accuracy and efficiency of analysis of incorporation, metabolism and excretion of a candidate compound for a pharmaceutical agent in hepatocytes, leading to a highly efficient drug discovery process.

DESCRIPTION OF SYMBOLS

A: Culturing device;
B, C: Compound test device;
1, 101: Compound-supplying section;
2, 102: Main body section;
3, 103: Collection section;
11: Gas-permeable membrane;
11': Partition wall;
12: Collagen coating layer;
13: Hepatocytes;
14: Bile canaliculus;
15: Collagen matrix;
16: Culture medium;
21: Gas-permeable membrane;
22: Collagen;
23: Hepatocytes;
24: Bile canaliculus;
25: Extracellular matrix;
26: Semipermeable membrane;
27: Passage; and
28: Tubular body.

The invention claimed is:

1. A method for producing cultured hepatocytes to form one or more bile canaliculi, comprising disposing hepatocytes embedded in an extracellular matrix on a gas-permeable membrane and culturing said hepatocytes while supplying oxygen from a gas-permeable membrane side, wherein a surface of said gas-permeable membrane is coated with collagen and said hepatocytes embedded in an extracellular matrix are disposed on the collagen-coated side of said gas-permeable membrane, and wherein said extracellular matrix constitutes a groove(s) or hollow, and said hepatocytes are disposed in said groove(s) or hollow, the width of the groove or hollow is not less than 30 μm and not more than 70 μm, and wherein one or more canaliculi are formed by the cultured hepatocytes.

2. A method for evaluating metabolism of a compound, comprising:
   (a) disposing hepatocytes embedded in an extracellular matrix on a gas-permeable membrane and culturing said hepatocytes while supplying oxygen from a gas-permeable membrane side, wherein a surface of said gas-permeable membrane is coated with collagen and said hepatocytes embedded in an extracellular matrix are disposed on the collagen-coated side of said gas-permeable membrane, and wherein said extracellular matrix constitutes a groove(s) or hollow, and said hepatocytes are disposed in said groove(s) or hollow, the width of the groove or hollow is not less than 30 μm and not more than 70 μm, and wherein one or more canaliculi are formed;
   (b) contacting said cultured hepatocytes with a candidate compound; and,
   (c) evaluating metabolism of said compound in said cultured hepatocytes.

3. The method according to claim 1, wherein said gas-permeable membrane is placed to form a tubular shape.

4. The method according to claim 1, wherein said gas-permeable membrane is a polydimethylsiloxane membrane.

5. The method according to claim 1, wherein said gas-permeable membrane is a fluorocarbon membrane.

6. The method according to claim 1, wherein said collagen is coated by covalent bonding.

7. The method according to claim 1, wherein said extracellular matrix is a collagen gel or a reconstituted basement membrane preparation extracted from Engelbreth-Holm-Swarm mouse sarcoma cells.

8. The method according to claim 1, wherein said extracellular matrix is composed of one or more non-biological components.

9. The method according to claim 1, wherein the width of the groove or hollow is not less than 30 μm and not more than 50 μm.

* * * * *

UNITED STATES PATENT AND TRADEMARK OFFICE
CERTIFICATE OF CORRECTION

PATENT NO. : 8,906,644 B2
APPLICATION NO. : 13/392226
DATED : December 9, 2014
INVENTOR(S) : Hitoshi Matsui It is certified that error appears in the above-identified patent and that said Letters Patent is hereby corrected as shown below:

Title Page

In item (73), "MITSUBISHI CHEMICAL MEDIENCE CORPORATION" should read --LSI MEDIENCE CORPORATION--

Signed and Sealed this
Second Day of February, 2016

Michelle K. Lee
*Director of the United States Patent and Trademark Office*